(12) United States Patent
Jacobsen et al.

(10) Patent No.: US 7,521,518 B2
(45) Date of Patent: *Apr. 21, 2009

(54) ETHYLENE COPOLYMER COMPOSITIONS

(75) Inventors: Grant B. Jacobsen, Houston, TX (US); Fumio Matsushita, Kurashiki (JP); Lee Spencer, Pearland, TX (US); Peter L. Wauteraerts, Oostham (BE)

(73) Assignee: Dow Global Technologies, Inc., Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/341,235

(22) Filed: Jan. 13, 2003

(65) Prior Publication Data
US 2003/0120013 A1 Jun. 26, 2003

Related U.S. Application Data

(63) Continuation of application No. 08/857,816, filed on May 16, 1997, now Pat. No. 6,506,866, which is a continuation-in-part of application No. 08/555,436, filed on Nov. 9, 1995, now abandoned, which is a continuation-in-part of application No. 08/340,989, filed on Nov. 17, 1994, now abandoned, application No. 10/341,235, and a continuation-in-part of application No. 08/610,647, filed on Mar. 4, 1996, now Pat. No. 5,834,393, which is a continuation-in-part of application No. 08/402,437, filed on Mar. 10, 1995, now abandoned.

(51) Int. Cl.
*C08F 4/6592* (2006.01)
*C08F 210/16* (2006.01)
*C08L 23/08* (2006.01)

(52) U.S. Cl. .......................... 526/348; 526/160; 526/170; 526/339; 526/348.1; 521/142; 521/144; 428/364; 525/240

(58) Field of Classification Search ................. 526/348, 526/161, 172, 134, 160, 170, 339, 348.1; 525/240; 521/142, 144; 428/364
See application file for complete search history.

(56) References Cited

U.S. PATENT DOCUMENTS

| | | |
|---|---|---|
| 3,280,220 A | 10/1966 | Nelson |
| 3,645,992 A | 2/1972 | Elston |
| 3,660,530 A | 5/1972 | Hoblit |
| 4,230,831 A | 10/1980 | Sakurai et al. |
| 4,438,238 A | 3/1984 | Fukushima et al. |
| 4,530,914 A | 7/1985 | Ewen et al. |
| 4,542,199 A | 9/1985 | Kaminsky et al. |
| 4,547,551 A | 10/1985 | Bailey et al. |
| 4,798,081 A | 1/1989 | Hazlitt et al. |
| 4,937,299 A | 6/1990 | Ewen et al. |
| 5,008,204 A | 4/1991 | Stehling |
| 5,026,797 A | 6/1991 | Takahashi et al. |
| 5,055,438 A | 10/1991 | Canich |
| 5,057,475 A | 10/1991 | Canich et al. |
| 5,064,802 A | 11/1991 | Stevens et al. |
| 5,089,321 A | 2/1992 | Chum et al. |
| 5,091,352 A | 2/1992 | Kioka et al. |
| 5,096,867 A | 3/1992 | Canich |
| 5,132,380 A | 7/1992 | Stevens et al. |
| 5,147,949 A | 9/1992 | Chang |
| 5,183,867 A | 2/1993 | Welborn, Jr. |
| 5,189,106 A | 2/1993 | Morimoto et al. |
| 5,189,192 A | 2/1993 | LaPointe et al. |
| 5,218,071 A | 6/1993 | Tsutsui et al. |
| 5,220,100 A | 6/1993 | Massie et al. |
| 5,227,440 A | 7/1993 | Canich et al. |
| 5,240,894 A | 8/1993 | Burkhardt et al. |
| 5,246,783 A | 9/1993 | Spenadel et al. |
| 5,260,384 A | 11/1993 | Morimoto et al. |
| 5,272,236 A | 12/1993 | Lai et al. |
| 5,278,272 A | 1/1994 | Lai et al. |
| 5,322,728 A | 6/1994 | Davey et al. |
| 5,374,696 A | 12/1994 | Rosen et al. |
| 5,380,810 A | 1/1995 | Lai et al. |
| 5,382,630 A * | 1/1995 | Stehling et al. .............. 525/240 |
| 5,384,299 A | 1/1995 | Turner et al. |
| 5,453,410 A | 9/1995 | Kolthammer et al. |
| 5,494,874 A | 2/1996 | Rosen et al. |
| 5,525,679 A | 6/1996 | Effler, Jr. et al. |
| 5,532,394 A | 7/1996 | Rosen et al. |
| 5,536,796 A | 7/1996 | Jejelowo et al. |

(Continued)

FOREIGN PATENT DOCUMENTS

CA  2150890  12/1995

(Continued)

OTHER PUBLICATIONS

Worldwide Metallocene Conference (Metcon) May 26-28, 1993, Houston, TX (1993), pp. 171-172 and 235-244.*

(Continued)

*Primary Examiner*—Roberto Rábago

(57) ABSTRACT

Disclosed is a novel ethylene copolymer by copolymerizing an ethylene and at least one comonomer selected from a compound represented by the formula $H_2C=CHR$ wherein R is an alkyl group or an aryl group, and a diene, by slurry polymerization process in the presence of a solid catalyst system comprising a support, a transition metal compound and an activator capable of converting the transition metal compound into a catalytically active transition metal complex.

12 Claims, No Drawings

U.S. PATENT DOCUMENTS

| | | | |
|---|---|---|---|
| 5,565,521 | A | 10/1996 | Effler, Jr. et al. |
| 5,582,923 | A | 12/1996 | Kale et al. |
| 5,602,067 | A | 2/1997 | Nowlin et al. |
| 5,631,069 | A | 5/1997 | Wooster et al. |
| 5,665,800 | A | 9/1997 | Lai et al. |
| 5,719,095 | A | 2/1998 | Brekner et al. |
| 5,723,705 | A | 3/1998 | Herrmann et al. |
| 5,756,607 | A | 5/1998 | Lux et al. |
| 5,763,547 | A * | 6/1998 | Kolthammer et al. ....... 526/129 |
| 5,773,155 | A | 6/1998 | Kale et al. |
| 5,801,113 | A | 9/1998 | Jejelowo et al. |
| 5,834,393 | A | 11/1998 | Jacobsen et al. |
| 5,844,045 | A | 12/1998 | Kolthammer et al. |
| 5,908,679 | A | 6/1999 | Berthold et al. |
| 6,043,180 | A | 3/2000 | Jacobsen et al. |
| 6,194,520 | B1 | 2/2001 | Cheruvu et al. |
| 6,462,161 | B1 * | 10/2002 | Cady et al. ................. 526/348 |
| 6,469,103 | B1 | 10/2002 | Jain et al. |
| 6,506,866 | B2 * | 1/2003 | Jacobsen et al. ............ 526/348 |
| 6,552,148 | B1 | 4/2003 | Cheung et al. |
| 6,787,608 | B2 | 9/2004 | VanDun et al. |
| 7,129,296 | B2 * | 10/2006 | Van Dun et al. ............ 525/191 |
| 7,153,909 | B2 * | 12/2006 | Van Dun et al. ............ 525/240 |
| 7,166,676 | B2 * | 1/2007 | Jacobsen et al. ............ 525/240 |
| 2004/0266966 | A1 | 12/2004 | Schramm et al. |
| 2006/0276593 | A1 | 12/2006 | Van Dun et al. |

FOREIGN PATENT DOCUMENTS

| | | | |
|---|---|---|---|
| DE | 3127133 | * | 1/1983 |
| DE | 3127133 A1 | | 1/1983 |
| EP | 0 022 376 | | 1/1981 |
| EP | 022 376 | * | 1/1981 |
| EP | 0 117 492 | | 9/1984 |
| EP | 0 022 376 B1 | | 3/1987 |
| EP | 0285443 A1 | | 10/1988 |
| EP | 416 815 | * | 3/1991 |
| EP | 416815 | | 3/1991 |
| EP | 0 435 514 | | 7/1991 |
| EP | 435 514 | * | 7/1991 |
| EP | 0 439 964 | | 8/1991 |
| EP | 439 964 | * | 8/1991 |
| EP | 0 447 035 | | 9/1991 |
| EP | 447 035 | * | 9/1991 |
| EP | 0515132 A2 | | 11/1992 |
| EP | 0368644 | | 12/1992 |
| EP | 0516458 A2 | | 12/1992 |
| EP | 545152 A1 | | 6/1993 |
| EP | 0 572 003 A2 | | 12/1993 |
| EP | 0 572 990 A2 | | 12/1993 |
| EP | 0578838 A1 | | 1/1994 |
| EP | 0582480 A2 | | 2/1994 |
| EP | 776 909 | * | 6/1997 |
| EP | 776909 A1 | | 6/1997 |
| EP | 783 022 | * | 7/1997 |
| EP | 783022 A1 | | 7/1997 |
| EP | 1198484 B1 | | 4/2002 |
| EP | 0 776 909 B1 | | 11/2003 |
| EP | 0 783 022 B1 | | 9/2004 |
| JP | 61-221245 | * | 1/1986 |
| JP | 61-57638 | * | 3/1986 |
| JP | 6-207059 | * | 7/1994 |
| JP | 6-329848 | * | 11/1994 |
| JP | 6-329848 | | 11/1996 |
| WO | WO-89/02453 | | 3/1989 |
| WO | WO89/02453 | * | 3/1989 |
| WO | WO91/09882 | * | 11/1991 |
| WO | WO-91/09882 | | 11/1991 |
| WO | WO 93/07187 | | 4/1993 |
| WO | WO 93/07188 | | 4/1993 |
| WO | WO 93/07189 | | 4/1993 |
| WO | WO 93/11172 | | 6/1993 |
| WO | WO-93/19104 | | 9/1993 |
| WO | WO-94/03506 | | 2/1994 |
| WO | WO 94/17112 | | 8/1994 |
| WO | WO 94/21691 | | 9/1994 |
| WO | WO 94/25523 | | 11/1994 |
| WO | WO95/00526 | * | 1/1995 |
| WO | WO-95/00526 | | 1/1995 |
| WO | WO 95/05419 | | 2/1995 |
| WO | WO-95/12622 | | 5/1995 |
| WO | WO 95/30713 | | 11/1995 |
| WO | WO-96/16092 | | 5/1996 |
| WO | WO 96/28480 | | 9/1996 |
| WO | WO 96/35750 | | 11/1996 |
| WO | WO-97/29152 | | 8/1997 |

OTHER PUBLICATIONS

Williams et al., Journal of Polymer Science, Polymer Letters (1968) p. 621, vol. 6.*
E. Plati et al., Polymer Engineering and Science, (Jun. 1975) pp. 470-477, vol. 15, No. 6.*
M.J. Cawood et al., Polymer Testing 1 (1980), pp. 3-7.*
X. Lu et al., Polymer Testing II (1992), pp. 309-319.*
Wild et al., Journal of Polymer Science, Polymer Physics Edition (1982), p. 441, vol. 20.*
Wikipedia article "Geosynthetic," http://en.wikipedia.org, Oct. 13, 2007.*
Zhou et. al., *Polymer*, (1993), p. 2520, vol. 34.
Bohm et al., *Advanced Materials*, (1992), p. 234, No. 3.
Worldwide Metallocene Conference (Metcon) May 26-28, 1993, Houston, Texas, (1993), pp. 171-172 and pp. 235-244.
Proceedings of 5th International Business Forum on Specialty Polyolefins Sep. 20-22, 1995, Houston, Texas, (1995), pp. 341-352.
Williams et al., *Journal of Polymer Science, Polymer Letters*, (1968), p. 621, vol. 6.
E. Plati et al., *Polymer Engineering and Science*, (Jun. 1975), pp. 470-477, vol. 15, No. 6.
M.J. Cawood et al., *Polymer Testing 1*, (1980), pp. 3-7.
X. Lu et al., *Polymer Testing II*, (1992), pp. 309-319.
Wild et al., *Journal of Polymer Science, Polymer Physics Edition*, (1982), p. 441, vol. 20.
"Cross Fractionation Chromatograph" catalog from Mitsubishi Chemical Corporation, 1998.
"*INSITE*" Technology in Gas and Slurry-Phase Polyethylene, by James K. Pierce, presentation to the European Patent Office, Apr. 2, 1998.

* cited by examiner

ETHYLENE COPOLYMER COMPOSITIONS

CROSS REFERENCE TO RELATED APPLICATIONS

This application is a continuation of patent application Ser. No. 08/857,816, filed on May 16, 1997, now U.S. Pat. No. 6,506,866, which is a continuation-in-part of application Ser. No. 08/555,436 filed on Nov. 9, 1995, now abandoned, which is a continuation-in-part of application Ser. No. 08/340,989 filed on Nov. 17, 1994 now abandoned; and a continuation-in-part of application Ser. No. 08/610,647 filed on Mar. 4, 1996, now U.S. Pat. No. 5,834,393, which is a continuation-in-part of application Ser. No. 08/402,437 filed on Mar. 10, 1995 now abandoned, all of which are incorporated by reference herein.

STATEMENT REGARDING FEDERALLY SPONSORED RESEARCH OR DEVELOPMENT

Not Applicable

REFERENCE TO MICROFICHE APPENDIX

Not applicable.

BACKGROUND OF THE INVENTION

The present invention relates to a novel ethylene copolymer and a method for producing the same. More particularly, the present invention is concerned with a novel ethylene copolymer comprising a copolymer of ethylene with at least one comonomer selected from the group comprising compounds represented by the formula $H_2C=CHR$ wherein R represents a $C_1$-$C_{20}$ linear, branched or cyclic alkyl group or a $C_6$-$C_{20}$ aryl group, and a $C_4$-$C_{20}$ linear, branched or cyclic diene, and having a specific density, and having not only a specific molecular weight distribution characteristic but also a specific comonomer content distribution characteristic.

The ethylene copolymer of the present invention has great advantages which have not been provided by conventional ethylene copolymers, i.e., it contains no impurities such as a wax, a gel and the like. In addition both the ethylene copolymer of the present invention and blend compositions therefrom also have excellent properties, such as high impact strength and excellent environmental stress cracking resistance, such that they can be advantageously used for the production of laminate films, blow-molded articles, pipes, coating materials for electric transmission cables, and the like.

Prior Art

Ethylene copolymers are widely used in various application fields, such as the production of films, blow-molded products, pipes and coating materials for electric transmission cables. With respect to any of these applications, it is required that an ethylene copolymer not only contain few impurities, such as wax, gels and the like, but also exhibit excellent properties, such as high impact strength and high environmental stress cracking resistance (hereinafter, frequently referred to as "ESCR properties"). However attempts to vary the molecular structure of a polymer to cause an improvement in one such property often results in a loss of performance in another. For instance polymers exhibiting high stiffness and heat resistance should have high crystallinity and low comonomer content, however this can cause a loss of toughness, ESCR, low optical properties and poor heat seal performance. Similarly for improved polymer processability (low extrusion amp and back pressure and no melt fracture) it is desirable to use polymers having a low molecular weight, and a broad molecular weight distribution with significant levels of long chain branching. However broad molecular weight distribution, especially at low polymer molecular weight, often causes wax buildup on the die, smoke generation on the extruder, and taste and odor problems in the resulting fabricated articles.

It is known that improvement in impact and environmental stress crack resistance of an ethylene copolymer, can be achieved by decreasing the comonomer content of the low molecular weight fraction of the ethylene copolymer to a level as low as possible while increasing the comonomer content of the high molecular weight fraction of the ethylene copolymer to a level as high as possible. It has also been demonstrated (as for example by Zhou et al, Polymer, Vol 24, p. 2520 (1993)) that large strain properties such as toughness, tear, impact and ESCR can also be improved by the presence of "tie molecules" in the resin. High molecular weight molecules with the highest comonomer content (i.e. the highest degree of short chain branching) are responsible for the formation of most of the tie molecules upon crystallization.

Thus it would be highly desirable for a copolymer to have a specific comonomer content distribution characteristic, wherein, in one aspect, the lower the molecular weight of a copolymer fraction in a molecular weight distribution of said copolymer, the lower the comonomer content of the copolymer fraction; and, in the other aspect, the higher the molecular weight of a fraction of said copolymer, the higher the comonomer content of the copolymer fraction.

However, in ethylene copolymers which are produced using a conventional Ziegler-Natta catalyst, it is likely that the lower the molecular weight of a copolymer fraction, the higher its comonomer content. Thus, such conventional ethylene copolymers have a comonomer content distribution which is completely contrary to the above-mentioned desired comonomer content distribution. Therefore, such conventional ethylene copolymers are at a disadvantage with respect to desirable properties, such as improved impact strength and ESCR.

Attempts to maximize toughness, modulus, impact strength and ESCR of ethylene copolymers has resulted in the preparation and use of blend compositions made out of two or more ethylene copolymer components of differing molecular structures. In addition to separately blending selected individual polymer components after their manufacture and isolation (so called "off-line" blending), such compositions can also be prepared by a method in which a copolymerization of ethylene with a comonomer is conducted by a multi-stage polymerization, using a plurality of different polymerization reactors, capable of providing different copolymerization conditions. This allows so called "in reactor" or "in process" production of ethylene copolymers comprising a mixture of a low molecular weight copolymer component, having a low comonomer content, and a high molecular weight copolymer component having a high comonomer content.

Such blend compositions containing solely Ziegler catalyst products are described in a number of patents. For example, Nelson (U.S. Pat. No. 3,280,220, Phillips Petroleum) teaches that a blend of an ethylene homopolymer of low molecular weight (formed in a solution process) and an ethylene/butene-1 copolymer of high molecular weight (formed in a particle forming process) provides higher ESCR and is more advantageous for containers and pipe than other such blends.

Hoblitt et al. (U.S. Pat. No. 3,660,530, the Dow Chemical Company) teaches a method where part of a homopolymer produced after a first reaction step is subjected to 1-butene. The still active catalyst then produces a block copolymer of polyethylene and polymerized butene-1. Both components are then admixed. The resultant blend has improved ESCR properties.

Fukushima et al. (U.S. Pat. No. 4,438,238) disclose blends consisting of components with densities between 0.910 and 0.940 g/cm$^3$ and broad molecular weight distributions with the polymers having substantially no long chain branches. These blends were found to have processability similar to that of high pressure polyethylene Bailey et al. (U.S. Pat. No. 4,547,551) teach that ethylene polymer blends of a high molecular weight ethylene polymer, preferably an ethylene/□-olefin copolymer, and a low molecular weight ethylene polymer, preferably an ethylene homopolymer, both preferentially having a narrow molecular weight distribution and low levels of long chain branching, exhibit excellent film properties and a better balance of stiffness and impact and ESCR, than expected for polyethylene of comparable density and flow.

Morimoto et al. (U.S. Pat. Nos. 5,189,106, and 5,260,384) disclose blends consisting of a high molecular weight copolymer in combination with a low molecular weight homopolymer having good processability and excellent low temperature mechanical properties.

Boehm et al., (Advanced Materials 4 (1992) no 3, p 237), disclose the cascade polymerization process in which the comonomer is introduced in the high molecular weight fraction of the polymer resulting in a larger amount of comonomer being present at the same overall density. This in turn results in a polymer composition having improved rigidity-lifetime (failure time) compared to conventional unimodal copolymers. Several patents have also appeared teaching the process to produce such materials in such cascade processes including EP 0 022 376 (Morita et al).

Unexamined Japanese Patent Application Laid-Open Specification Nos. 61-221245 and 61-57638, disclose attempts to increase the comonomer content of high molecular weight copolymer fractions by a method in which a low molecular weight polymer having a low comonomer content and a high molecular weight polymer having a high comonomer content are separately produced and blended by means of a kneader, or a method in which a copolymerization of ethylene with a comonomer is conducted by multi-stage polymerization, thereby producing an ethylene copolymer comprising a mixture of a low molecular weight polymer component having a low comonomer content and a high molecular weight polymer component having a high comonomer content.

Finally, Sakurai et al (U.S. Pat. No. 4,230,831) disclose that it is beneficial to mix low density polyethylene with various blend compositions to improve polymer die swell or melt tension.

In single component ethylene copolymers produced by employing a Ziegler catalyst, some improvement is achieved with respect to impact resistance and ESCR properties. Such ethylene copolymers, however, inherently exhibit not only a broad molecular weight distribution but also a broad tail on both the low and high molecular weight side of the molecular weight distribution. The presence of the low molecular weight material can disadvantageously lead to wax formation. On the other hand, the high molecular weight material can disadvantageously lead to gel formation.

In addition, blend compositions which are a mixture of such ethylene copolymers produced by a Ziegler catalyst, may comprise component copolymers which are completely different from each other in properties, i.e., a low molecular weight polymer component having a low comonomer content and a high molecular weight polymer component having a high comonomer content. This can lead to the component polymers undergoing phase separation such that the dispersion of the component polymers becomes non-uniform, and thus not only does the ethylene copolymer become non-uniform in properties but also gel formation occurs.

As an alternative to the use of Ziegler-Natta catalysts, the use of metallocene catalysts has recently been proposed (DE 31271332) and commercialized. As disclosed in, for example, Worldwide Metallocene Conference (Metcon) '93 May 26-28, Houston Tex., p. 171-172 and p. 235-244 (1993) and Proceedings of 5th International Business Forum on Specialty Polyolefins '95, September 20-22, Houston Tex., p. 341-352 (1995), an ethylene copolymer produced using such a metallocene catalyst has characteristics such that both a low molecular weight fraction and a high molecular weight fraction have approximately the same comonomer content, and that the comonomer content distribution is almost uniform across the molecular weight distribution of the copolymer. That is, an ethylene copolymer produced using a metallocene catalyst has a more uniform comonomer content distribution than that of an ethylene copolymer produced using a Ziegler-Natta catalyst. On the other hand, however, ethylene copolymers produced using a metallocene catalyst are still unsatisfactory with respect to desired improvements in impact resistance and ESCR properties of products of such copolymers.

Again, as was the case with Ziegler catalyst products, attempts to improve properties such as ESCR and impact resistance of products of metallocene catalysts have included their incorporation into blend compositions. A number of techniques have been proposed to prepare such blends, including a method in which two or more different ethylene copolymers having different comonomer contents are separately produced and blended by means of a kneader or a method in which an ethylene copolymer comprised of a mixture of two or more different ethylene copolymer components having different comonomer contents is produced by multi-stage polymerization (see, for example, EP 0 447 035). Further, it has also been proposed to use a method in which a mixture of two or more different types of metallocene catalysts is used to produce an ethylene copolymer comprised of a mixture of two or more different ethylene copolymer components having different comonomer contents (see, for example, U.S. Pat. Nos. 4,937,299 and 4,530,914).

However, an ethylene copolymer produced using a metallocene catalyst typically has a very narrow molecular weight distribution ($M_w$/Mn) of approximately 2. Therefore, when two different types of copolymers, namely a low molecular weight copolymer and a high molecular weight copolymer which are extremely different in molecular weight from each other, are produced using different metallocene catalysts, the respective amounts of copolymer chains having common molecular weights is very small in the two different copolymers, so that the compatibility between these two different copolymers is very poor.

In order to solve the above-mentioned problem, a method in which an ethylene copolymer produced using a metallocene catalyst is blended with an ethylene copolymer produced using a Ziegler-Natta catalyst has been proposed, for example, in EP 0 439 964 and EP 0 435 514. Further, a method in which an ethylene copolymer produced using a metallocene catalyst is blended with an ethylene copolymer produced by a high pressure polymerization process has been disclosed, for example, in Unexamined Japanese Patent Application Laid-Open Specification Nos. 6-207059 and 6-329848.

However there remains a requirement to produce an ethylene copolymer which not only contains few impurities such as wax, gels and the like, but also has excellent properties, including high impact strength and excellent ESCR. There also remains a requirement to develop an ethylene copolymer which contains no impurities such as a wax, a gel and the like while simultaneously exhibiting the above-mentioned desired comonomer content distribution, namely, in one aspect, the lower the molecular weight of a copolymer fraction, the lower the comonomer content of the copolymer fraction; and, in the other aspect, the higher the molecular weight of a copolymer fraction, the higher the comonomer content of the copolymer fraction.

There also remains a requirement to produce blend compositions comprising said ethylene copolymers which also have excellent properties, such as high impact strength and excellent ESCR properties. Finally there also remains a requirement for producing blend compositions with good compatibility between the two components and exhibiting improved uniformity and balance in properties while having low wax content and low tendency for gel formation.

SUMMARY OF THE INVENTION

It has surprisingly been found that such a required ethylene copolymer can be produced using the the specific polymerization and process of the present invention.

Accordingly, it is one object of the present invention to provide a novel ethylene copolymer which not only contains substantially no impurities such as a wax, a gel and the like, but also exhibits a comonomer content distribution in which the lower the molecular weight of a fraction of said copolymer the lower the comonomer content and the higher the molecular weight of a fraction of said copolymer the higher the comonomer content.

The foregoing and other objects, features and advantages of the present invention will become apparent to those skilled in the art from the following detailed description and appended claims.

BRIEF DESCRIPTION OF THE DRAWINGS

Not applicable.

DETAILED DESCRIPTION OF THE INVENTION

Definitions.

All references herein to elements or metals belonging to a certain Group refer to the Periodic Table of the Elements published and copyrighted by CRC Press, Inc., 1989. Also any reference to the Group or Groups shall be to the Group or Groups as reflected in this Periodic Table of the Elements using the IUPAC system for numbering groups.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The term "hydrocarbyl" as employed herein means any aliphatic, cycloaliphatic, aromatic, aryl substituted aliphatic, aryl substituted cycloaliphatic, aliphatic substituted aromatic, or aliphatic substituted cycloaliphatic groups and any combination thereof.

The term "hydrocarbyloxy" means a hydrocarbyl group having an oxygen linkage between it and the carbon atom to which it is attached.

The term "silyl" means a group having a silicon linkage between it and the carbon atom to which it is attached.

The term "germyl" means a group having a germanium linkage between it and the carbon atom to which it is attached.

The term "substituted cyclopentadienyl" is intended to include ring-substituted or polynuclear derivatives of the cyclopentadienyl moiety wherein the substituent is hydrocarbyl, hydrocarbyloxy, hydrocarbylamino, cyano, halo, silyl, germyl, siloxy or mixtures thereof or two such substituents are a hydrocarbylene group, the substituent (or two substituents together) having up to 30 non-hydrogen atoms. Specific examples of substituted cyclopentadienyls include indenyl, tetrahydroindenyl, fluorenyl, and octahydrofluorenyl groups.

The term "Bronsted Acid cation" means a cation which acts as a proton donor.

The term "interpolymer" is used herein to indicate a polymer wherein at least two different monomers are polymerized to make the interpolymer. This includes copolymers, terpolymers, etc.

Test Methods.

Melt Flow and Density Measurements.

The density of the polymer compositions for use in the present invention was measured in accordance with ASTM D-792.

The molecular weight of the polymer compositions for use in the present invention is conveniently indicated using a melt index measurement according to ASTM D-1238, Condition 190° C./2.16 kg (formally known as "Condition (E)" and also known as $I_2$) was determined, as were conditions 190° C./5 kg, 10 kg and 21.6 kg known as $I_5$, $I_{10}$, and $I_{21}$ respectively. Melt index is inversely proportional to the molecular weight of the polymer. Thus, the higher the molecular weight, the lower the melt index, although the relationship is not linear. Melt flow ratios were taken from any pair of these values.

Other useful physical property determinations made on the novel polymer compositions described herein include the melt flow ratio (MFR): measured by determining "$I_{10}$" (according to ASTM D-1238, Condition 190° C./10 kg (formerly known as "Condition (N)") and dividing the obtained $I_{10}$ by the $I_2$. The ratio of these two melt index terms is the melt flow ratio and is designated as $I_{10}/I_2$. Other melt flow ratios measured include $I_{21.6}/I_5$, and $I_{21.6}/I_2$.

Molecular Weight and Distribution Measurements.

The molecular weight ($M_w$) and distribution ($M_w/M_n$) of the polymers of the present invention were determined by gel permeation chromatography (GPC) on a Waters 150 C. high temperature chromatographic unit equipped with mixed porosity columns, operating at a system temperature of 140° C. The solvent was 1,2,4-trichlorobenzene, from which 0.3 percent by weight solutions of the samples were prepared for injection. The flow rate was 1.0 milliliters/minute and the injection size was 100 microliters.

The molecular weight determination was deduced by using narrow molecular weight distribution polystyrene standards (from Polymer Laboratories) in conjunction with their elution volumes. The equivalent polyethylene molecular weights were determined by using appropriate Mark-Houwink coefficients for polyethylene and polystyrene (as described by Williams and Ward in *Journal of Polymer Science, Polymer Letters*, Vol. 6, (621) 1968) to derive the following equation:

$$M_{polyethylene} = a*(M_{polystyrene})^b.$$

In this equation, a=0.4316 and b=1.0. Weight average molecular weight, $M_w$, and number average molecular weight, $M_n$, was calculated in the usual manner according to the following formula:

$$Mj = (\Sigma w_i(M_i^j))^j;$$

where $w_i$ is the weight fraction of the molecules with molecular weight $M_i$ eluting from the GPC column in fraction i and j=1 when calculating $M_w$ and j=−1 when calculating $M_n$.

Tensile Properties.

The tensile properties of the molded materials were measured in accordance with ASTM D 638-76. Tensile strength, yield, toughness and 2% secant modulus of the films was measured in accordance with ASTM D-882; PPT tear was measured in accordance with ASTM D-2582.

Modulus of Elasticity.

The modulus of elasticity of the materials was measured in accordance with ISO 527.

Viscosity Number.

The viscosity number of the materials in decaline was measured in accordance with ISO 1191.

Haze.

Haze was measured on a 0.5 mm thick compression molded specimen according to ASTM D 1003.

Impact Strength.

The Double-V notched impact strength of the materials was measured in accordance with DIN 53753 (1J pendulum).

Impact Properties.

The impact properties were evaluated in accordance with JIS-K7 111.

Critical Strain Energy Release Rate.

The critical strain energy release rate $G_C$ was measured in the Charpy mode, in accordance with the procedure described by E. Plati and J. G. Williams in Polymer Engineering and Science, June, 1975, Volume 15, No 6, pp. 470 to 477. For each temperature at least 6 samples are used. The sample dimensions are 125 mm×10 mm×10 mm. The bars are machined out of thick compression molded sheets. The procedure used to mold these sheets was a modification of the procedure outlined in "A compression molding technique for thick sheets of thermoplastics" by M. J. Cawood and G. A. H. Smith in Polymer Testing 1 (1980), 3-7.

Thus the polymer granules or powders were compression molded in a 10 mm thick mold, laterally insulated using Teflon™. They were heated up to 160° C. and kept at 6.7 MPa for three minutes followed by three one minute cycles of exertion and release. Excessive flash was removed. The material was then heated to 180° C. and kept for about 5 minutes at 6.7 MPa, which was also exerted and released for 3 cycles of one minute each. Finally the melt was solidified under a pressure of 1.7 MPa and slowly cooled overnight by switching of the heating.

Bending ESCR Test.

The Bending ESCR Test was carried out in 10 wt % of surface-active agent solution in accordance with JIS-K6760. The testing temperature was 50° C. or 80° C. Pennsylvania Notch Test (PENT).

The Pennsylvania Notch Test is a slow crack growth test, performed following the procedure described by X. Lu and N. Brown, Polymer Testing 11 (1992), pages 309319. The test is conducted at 2.4 MPa and 80° C. The sample dimensions are 50 mm×25 mm×10 mm and are machined from the same sheet as the $G_C$ bars.

Rheological Parameters.

Viscosities were measured on an Rheometrics mechanical spectrometer at 190° C. in the oscillatory mode.

Infrared Analysis.

Comonomer content was measured using infrared spectroscopy on a Beckman IR2450 Spectrophotometer.

Intrinsic Tear.

Intrinsic tear was measured on the compression molded sheet using the Elmendorf tear (type B) method as described in ASTM D-1922.

Determination of the Slope of Strain Hardening Coefficient.

The slope of strain hardening is measured by compression molding a plaque from the polymer to be tested. Typically, the plaque is molded at about 177° C. for 4 minutes under almost no pressure and then pressed for 3 minutes under a pressure of about 200 psi. The plaque is then allowed to cool at about 8° C./minute while still under 200 psi pressure. The molded plaque has a thickness of about 0.005 inches. The plaque is then cut into a dogbone shaped test piece using a steel rule die. The test piece is 0.315 inches wide and 1.063 inches long. The start of the curved portion of the dogbone shape begins at 0.315 inches from each end of the sample and gently curves (i.e., tapers) to a width of 0.09 inches. The curve ends at a point 0.118 inches from the start of the curve such that the interior portion of the dogbone test piece has a width of 0.09 inches and a length of 0.197 inches.

The tensile properties of the test sample is tested on an Instron Tensile Tester at a crosshead speed of 1 inch/minute. The slope of strain hardening is calculated from the resulting tensile curve by drawing a line parallel to the strain hardening region of the resulting stress/strain curve. The strain hardening region occurs after the sample has pulled its initial load ((i.e., stress) usually with little or no elongation during the intial load) and after the sample has gone through a slight drawing stage (usually with little or no increase in load, but with increasing elongation (i.e., strain)). In the strain hardening region, the load and the elongation of the sample both continue to increase. The load increases in the strain hardening region at a much lower rate than during the intial load region and the elongation also increase, again at a rate lower than that experienced in the drawing region. The slope of the parallel line in the strain hardening region is then determined.

The slope of strain hardening coefficient (SHC) is calculated according to the following equation:

$$SHC = (\text{slope of strain hardening})*(I_2)^{0.25}$$

where $I_2$=melt index in grams/10 minutes.

The Ethylene Copolymer.

In one aspect of the present invention, there is provided an ethylene copolymer comprising a copolymer of ethylene with at least one comonomer selected from the group consisting of a compound represented by the formula $H_2C=CHR$ wherein R is a $C_1$-$C_{20}$ linear, branched or cyclic alkyl group or a $C_6$-$C_{20}$ aryl group, and a $C_4$-$C_{20}$ linear, branched or cyclic diene, prepared by a process copolymerizing said ethylene with said comonomer by slurry polymerization in the presence of a solid catalyst system comprising: a support, a transition metal compound, and an activator capable of converting the transition metal compound into a catalytically active transition metal complex; and wherein said ethylene copolymer has the following properties (1) to (5):

(1) a density d (g/cm$^3$) of from 0.870 to 0.980;

(2) an $M_w$/Mn of from 2.5 to 10, wherein $M_w$ and $M_n$ are, respectively, a weight average molecular weight and a number average molecular weight, both as measured by gel permeation chromatography (GPC), in addition, the Mw/Mn satisfies the following inequalities;

$$1.25 \log M_w - 2.5 \leq M_w/M_n \leq 3.5 \log Mw - 11.0;$$

(3) when, in cross fractionation chromatography (CFC) of the ethylene copolymer, with respect to extraction at an arbitrary temperature T(° C.) falling within the range of between a first temperature at which a maximum amount of extraction is exhibited and a second temperature which is 10° C. higher than the first temperature, the relationship between the arbitrary temperature T(° C.) and a point in molecular weight on a molecular weight distribution profile of a copolymer fraction extracted at the arbitrary temperature T(° C.) at which point in molecular weight the molecular weight distribution profile of the copolymer fraction shows a peak having a maximum intensity is treated by the least squares method to obtain an approximate straight line, the approximate straight line has a gradient within the range defined by the formula (I):

$$-1 \leq \{\log Mp(T^1) - \log Mp(T^2)\}/(T^1 - T^2) \leq -0.005 \quad (I)$$

wherein:

$T^1$ and $T^2$ are two different arbitrary extraction temperatures T(° C.) within the range of between the first temperature and the second temperature, and $Mp(T^1)$ and $Mp(T^2)$ are, respectively, molecular weights corresponding to $T^1$ and $T^2$ on the approximate straight line; and (4) the measurement of the ethylene copolymer by CFC shows characteristics such that the sum of respective amounts of copolymer fractions extracted at temperatures which are at least 10° C. lower than the first temperature as defined above is 8% by weight or less, based on the total amount of, excluding purge, copolymer fractions extracted at temperatures in the overall range of extraction temperatures in CFC;

(5) within a range in molecular weight of the ethylene copolymer which is defined by the formula (II):

$$\log(Mt) - \log(Mc) \leq 0.5 \quad (II)$$

wherein:

Mt is a point in molecular weight on a molecular weight distribution profile at which the profile shows a peak having a maximum intensity, and Mc is an arbitrary point in molecular weight on the molecular weight distribution profile; and the molecular weight distribution profile is obtained together with a comonomer content distribution profile by subjecting the ethylene copolymer to gel permeation chromatography/Fourier transformation infrared spectroscopy (GPC/FT-IR), wherein an approximate straight line obtained from the comonomer content distribution profile by the least squares method has a gradient within the range defined by the formula (III):

$$0.0005 \leq \{C(Mc^1) - C(Mc^2)\}/(\log Mc^1 - \log Mc^2) \leq 0.05 \quad (III)$$

wherein:

$Mc^1$ and $Mc^2$ are two different arbitrary points (Mc) in molecular weight which satisfy the formula (II), and $C(Mc^1)$ and $C(Mc^2)$ are, respectively, comonomer contents corresponding to $Mc^1$ and $Mc^2$ on the approximate straight line.

The ethylene copolymer of the present invention defined above is a novel ethylene copolymer having advantages in that it not only contains substantially no impurities such as a wax, a gel and the like, but also has excellent properties, such as high impact strength and excellent environmental stress cracking resistance.

In another aspect of the present invention, there is provided a process for producing the ethylene copolymer comprising a copolymer of ethylene with at least one comonomer selected from the group consisting of a compound represented by the formula $H_2C=CHR$ wherein R is a $C_1$-$C_{20}$ linear, branched or cyclic alkyl group or a $C_6$-$C_{20}$ aryl group, and a $C_4$-$C_{20}$ linear, branched or cyclic diene, which process comprises copolymerizing said ethylene with said comonomer by slurry polymerization in the presence of a solid catalyst system comprising: a support, a transition metal compound, and an activator capable of converting the transition metal compound into a catalytically active transition metal complex wherein said solid catalyst system comprises;

1) a supported catalyst component comprising (a) a support material, an organometal compound wherein the metal is selected form Groups 2-13 of the Periodic Table of the Elements, germanium, tin, and lead, and (b) an activator compound comprising (b-1) a cation which is capable of reacting with a transition metal compound to form a catalytically active transition metal complex, and (b-2) a compatible anion having up to 100 nonhydrogen atoms and containing at least one substituent comprising an active hydrogen moiety; and 2) a transition metal compound.

In still another aspect of the present invention, there is provided a process for producing the above-defined ethylene copolymer, wherein the transition metal compound contains at least one cyclic or noncyclic π-bonded anionic ligand group.

The ethylene copolymer of the present invention is a copolymer of ethylene with at least one comonomer selected from the group consisting of a compound represented by the formula $H_2C=CHR$ wherein R is a $C_1$-$C_{20}$ linear, branched or cyclic alkyl group or a $C_6$-$C_{20}$ aryl group, and a $C_4$-$C_{20}$ linear, branched or cyclic diene.

The ethylene copolymer of the present invention has a density d (g/cm$^3$) of from 0.870 to 0.980. Ethylene copolymers having a density d of lower than 0.870 g/cm cannot be produced very well by slurry polymerization. On the other hand, when an ethylene copolymer has a density d (g/cm$^3$) of higher than 0.980, the comonomer content of such a copolymer is too low, so that it is likely that the copolymer has substantially the same properties as those of an ethylene homopolymer, but does not have various excellent properties characteristic of a copolymer having a density d (g/cm$^3$) within the above-defined range. In the present invention, it is preferred that the ethylene copolymer have a density d (g/cm$^3$) of from 0.87 to 0.980, more preferably from 0.890 to 0.965, and most preferably from 0.915 to 0.955.

The ethylene copolymer of the present invention has an $M_w/M_n$ of from 2.5 to 10, wherein Mw and Mn are, respectively, the weight average molecular weight and the number average molecular weight, both as measured by gel permeation chromatography (GPC). The ratio $M_w/M_n$ is used as a criterion for molecular weight distribution. In the present invention, when an ethylene copolymer has an $M_w/M_n$ of smaller than 2.5, the molecular weight distribution of the copolymer is too narrow, so that it becomes difficult for the ethylene copolymer to have the specific comonomer content distribution characteristic defined in the present invention. On the other hand, when an ethylene copolymer has an $M_w/M_n$ of larger than 10, it is likely that the impact resistance of the copolymer becomes disadvantageously low. Further, in the present invention, it is preferred that the ethylene copolymers have an $M_w/M_n$ of from 2.8 to 8, more preferably from 3 to 7.

The ethylene copolymer in the present invention has a melt index, ($I_2$), of from about 0.0001 to about 10000, preferably from about 0.001 to about 5000, more preferably from about 0.01 to about 3000 g/10 min.

The $I_{21.6}/I_2$ ratio of the ethylene copolymer of the present invention is from about 15 to about 65, preferably from about 18 to about 55, more preferably from about 20 to about 50, or an $I_{10}/I_2$ ratio of from about 5 to about 30, preferably from about 5 to about 28, more preferably from about 5.5 to about 25.

With respect to the ethylene copolymer of the present invention, when, in cross fractionation chromatography (CFC) of the ethylene copolymer of the present invention, with respect to extraction at an arbitrary temperature T(° C.) falling within the range of between a first temperature at which a maximum amount of extraction is exhibited and a second temperature which is the lower temperature of either the temperature of 10° C. higher than said first temperature or 96° C., the relationship between the arbitrary temperature T(° C.) and a point in molecular weight on a molecular weight distribution profile of a copolymer fraction extracted at the arbitrary temperature T(° C.) at which point in molecular weight the molecular weight distribution profile of the copolymer fraction shows a peak having a maximum intensity is treated by the least squares method to obtain an approximate straight line within the range of between said first temperature and said second temperature; if there is the copolymer fraction the amount of which is less than 1% by weight on the total amount, excluding purge, of copolymer fraction extracted at temperatures in the overall range of extraction temperatures in CFC, the copolymer fraction can be excluded from the calculation for the approximate straight line; the approximate straight line has a gradient within the range defined by the formula(I):

$$-1 \leq \{\log Mp(T^1) - \log Mp(T^2)\}/(T^1 - T^2) \leq -0.005 \quad (I)$$

wherein:
T$^1$ and T$^2$ are two different arbitrary extraction temperatures T(° C.) within the range of between the first temperature and the second temperature, and
Mp(T$^1$) and Mp(T$^2$) are, respectively, molecular weights corresponding to T$^1$ and T$^2$ on said approximate straight line.

In the above formula (I), the term $\{\log Mp(T^1) - \log Mp(T^2)\}/(T^1 - T^2)$ indicates a gradient of the above-mentioned approximate straight line.

In the present invention, the cross fraction chromatography (CFC) is conducted using CFC T-150A (manufactured and sold by Mitsubishi Kagaku Corp., Japan). The measurement by CFC is conducted as follows. 20 mg of a sample is dissolved in 20 ml of dichlorobenzene having a temperature of 140° C., to thereby obtain a solution of the sample. Then, 5 ml of the obtained solution is added to a TREF (temperature rising elution fractionation) column filled with glass beads, and the solution is allowed to cool to 0° C. at a rate of 1° C./min. Subsequently, the solution is heated, so as to elevate the temperature of the solution at a rate of 1° C./min, thereby extracting copolymer fractions. Then, the extracted copolymer fractions are subjected to gel permeation chromatography (GPC) using a GPC column Shodex AD806MS (manufactured and sold by Showa Denko K.K., Japan), followed by Fourier transformation infrared spectroscopy (FT-IR) using Nicolet Manga-IR spectrometer 550 (manufactured and sold by Nicolet Co., Ltd., U.S.A.).

With respect to further details of the method for conducting CFC, reference can be made to the catalogue attached to the above-mentioned CFC T-150A.

With respect to conventional ethylene copolymers produced using a conventional Ziegler catalyst, the gradient $\{\log Mp(T^1) - \log Mp(T^2)\}/(T^1 - T^2)$ is generally almost 0 or of a positive value. With respect to conventional ethylene copolymers produced using conventional metallocene catalysts which have recently been being put into practical use, the gradient $\{\log Mp(T^1) - \log Mp(T^2)\}/(T^1 - T^2)$ is almost 0.

As already mentioned above, in the present invention, when, in cross fractionation chromatography (CFC) of the ethylene copolymer of the present invention, with respect to extraction at an arbitrary temperature T(° C.) falling within the range of between a first temperature at which a maximum amount of extraction is exhibited and a second temperature which is the lower temperature of either the temperature of 10° C. higher than said first temperature or 96° C., the relationship between the arbitrary temperature T(° C.) and a point in molecular weight on a molecular weight distribution profile of a copolymer fraction extracted at the arbitrary temperature T(° C.) at which point in molecular weight the molecular weight distribution profile of the copolymer fraction shows a peak having a maximum intensity is treated by the least squares method to obtain an approximate straight line, the approximate straight line has a gradient [i.e., $\{\log Mp(T^1) - \log Mp(T^2)\}/(T^1 - T^2)$] which has negative value. This means that the copolymer fraction extracted at a low temperature, i.e., a low density copolymer fraction having a high comonomer content, has a higher molecular weight than that of the copolymer fraction extracted at a high temperature, i.e., a high density copolymer fraction having a low comonomer content.

The ethylene copolymer of the present invention has a gradient [$\{\log Mp(T^1) - \log Mp(T^2)\}/(T^1 - T^2)$] which is considerably large in negative value (within the range of from −0.005 to −1). This clearly indicates that, in the ethylene copolymer of the present invention, a copolymer fraction having a high comonomer content has a high molecular weight, contrary to the conventional ethylene copolymers, in which a copolymer fraction having a high comonomer content typically has a low molecular weight.

Further, the ethylene copolymer of the present invention has a gradient [$\{\log Mp(T^1) - \log Mp(T^2)\}/(T^1 - T^2)$] in negative value within a range of from −0.005 to −1. This indicates that the copolymers having copolymer fractions of widely varied comonomer contents and widely varied molecular weights can be obtained within the above-mentioned range of the gradient, which copolymer fractions widely vary from a low molecular weight copolymer fraction having a low comonomer content, i.e., a high density copolymer fraction having a low molecular weight, to a high molecular weight copolymer fraction having a high comonomer content, i.e., a low density copolymer fraction having a high molecular weight. The copolymers of the present invention, which have different comonomer contents, exhibit excellent miscibility to each other or one another. Therefore, in the present invention, the copolymers having different comonomer contents can be blended, so as to obtain a copolymer having desired properties, without occurrence of gel formation.

However, when the gradient $[\{\log Mp(T^1)-\log Mp(T^2)\}/(T^1-T^2)]$ becomes too small, it becomes difficult to obtain a designed copolymer having a desired structure and properties. Therefore, in the present invention, the gradient must be −1 or more. Further, in the present invention, the gradient be preferably within the range defined by the formula:

$$-0.5 \leq \{\log Mp(T^1)-\log Mp(T^2)\}/(T^1-T^2) \leq -0.007;$$

preferably, $$-0.1 \leq \{\log Mp(T^1)-\log Mp(T^2)\}/(T^1-T^2) \leq -0.01;$$

more preferably, $$-0.08 \leq \{\log Mp(T^1)-\log Mp(T^2)\}/(T^1-T^2) \leq -0.02;$$

wherein $T^1$, $T^2$, $Mp(T^1)$ and $Mp(T^2)$ are as defined for the formula (I).

When the ethylene copolymer of the present invention is measured by CFC, the ethylene copolymer shows characteristics such that the sum of respective amounts of copolymer fractions extracted at temperatures which are at least 10° C. lower than the first temperature as defined above is 8% by weight or less, based on the total amount, excluding purge, of copolymer fractions extracted at temperatures in the overall range of extraction temperature in CFC. In the present invention, the above-mentioned sum of respective amounts of copolymer fractions can be obtained from an integral curve showing the amounts of extracted copolymer fraction, relative to extraction temperatures.

On the other hand, when conventional ethylene copolymers, produced using a Ziegler-Natta catalyst, are measured by CFC, the ethylene copolymers show characteristics such that a relatively large amount of copolymer fractions are extracted at temperatures which are at least 10° C. lower than the first temperature as defined above, as shown by Comparative Examples 4 through 6. This indicates that such ethylene copolymers have a broad distribution of composition and contains low molecular weight waxy components or extremely low density copolymer fractions.

Conventionally, it has been considered that the ethylene copolymers produced using metallocene catalysts, which have recently been being put into practical use, have a narrow distribution in comonomer content. However, when some of such ethylene copolymers are subjected to CFC measurement, a considerably large amount of copolymer fractions are extracted within a wide range of temperatures which are at least 10° C. lower than the first temperature as defined above.

In the case of the ethylene copolymer of the present invention, the amount of such copolymer fractions extracted at temperatures which are at least 10° C. lower than the first temperature as defined above are extremely small. Specifically, when the ethylene copolymer of the present invention is measured by CFC, the ethylene copolymer shows characteristics such that the sum of respective amounts of copolymer fractions extracted at temperatures which are at least 10° C. lower than the first temperature as defined above is 8% by weight or less, preferably 5% by weight or less, more preferably 3.5% by weight or less, based on the total amount of copolymer fractions extracted at temperatures in the overall range of extraction temperatures in CFC, but excluding the purge.

Due to such an extremely small content of the copolymer fractions extracted at temperatures which are at least 10° C. lower than the first temperature as defined above, the ethylene copolymer of the present invention has excellent properties, for example, a freedom of adverse effects caused by the presence of waxy components and low density copolymer fractions. Further, in the present invention, it is possible to produce copolymers having a very low density and a very low molecular weight. Such copolymers can be advantageously mixed for providing a wide variety of mixtures, each comprising two or more different copolymer components having different comonomer contents. Therefore, it becomes possible to design various mixtures having desired properties by the use of the above-mentioned copolymers having a very low density and a very low molecular weight. This is very advantageous from the commercial point of view.

In the present invention, within a range in molecular weight of the ethylene copolymer which is defined by the formula (II):

$$\log(Mt)-\log(Mc) \leq 0.5 \quad \text{(II)}$$

wherein:
Mt is a point in molecular weight on a molecular weight distribution profile at which the profile shows a peak having a maximum intensity, and
Mc is an arbitrary point in molecular weight on the molecular weight distribution profile,
the molecular weight distribution profile being obtained together with a comonomer content distribution profile by subjecting the ethylene copolymer to gel permeation chromatography/Fourier transformation infrared spectroscopy (GPC/FT-IR), an approximate straight line obtained from the comonomer content distribution profile by the least squares method has a gradient within the range defined by the formula (III):

$$0.0005 \leq \{C(Mc^1)-C(Mc^2)\}/(\log Mc^1-\log Mc^2) \leq 0.05 \quad \text{(III)}$$

wherein:
$Mc^1$ and $Mc^2$ are two different arbitrary points (Mc) in molecular weight which satisfy the formula (II), and
$C(Mc^1)$ and $C(Mc^2)$ are, respectively, comonomer contents corresponding to $Mc^1$ and $Mc^2$ on the approximate straight line.

As mentioned above, the molecular weight distribution profile and the comonomer content distribution profile can be obtained by subjecting the ethylene copolymer to gel permeation chromatography/Fourier transformation infrared spectroscopy (GPC/FT-IR). In the present invention, the measurement by GPC is conducted using 150C ALC/GPC (manufactured and sold by Waters Assoc. Co. U.S.A.), in which three columns [one Shodex AT-807S (manufactured and sold by Showa Denko K.K., Japan) and two TSK-gel GMH-H6 (manufactured and sold by Tosoh Corp., Japan)], which are connected in series, are used, and the measurement by FT-IR is conducted by dissolving 20 to 30mg of a sample in 15 ml of trichlorobenzene having a temperature of 140° C., and applying 500 to 1,000 µl of the resultant solution to a FT-IR apparatus (PERKIN-ELMER 1760X, manufactured and sold by Perkin Elmer Cetus, Co., Ltd., U.S.A.).

In the present invention, the comonomer content is defined as a value obtained by dividing the number of comonomer units relative to 1,000 methylene units contained in the copolymer, by 1,000. For example, when 5 comonomer units are contained relative to 1,000 methylene units, the comonomer content is 0.005. The value of the comonomer content can be obtained from the ratio of the intensity of an absorbance attributed to the comonomer units to the intensity of an absorbance attributed to the methylene units, which ratio can be obtained by FT-IR. For example, when a linear α-olefin is used as a comonomer, the ratio of the intensity of absorbance at 2,960 cm$^{-1}$, which is attributed to the methyl groups, to the intensity of absorbance at 2,925 cm$^{-1}$, which is attributed to the methylene groups, is obtained by FT-IR. From the obtained ratio, the comonomer content can be obtained.

Generally, the above-mentioned comonomer content distribution profile is shown as a line containing points indicating comonomer contents. For improving the accuracy of the profile, it is desirable to obtain a large number of points indicating the comonomer contents by repeatedly conducting the comonomer content measurement using the same sample under the same conditions. In the present invention, within the above-defined range in molecular weight of the ethylene copolymer, an approximate straight line is obtained from the obtained points of comonomer content distribution profile by the least squares method.

In the present invention, the gradient of the approximate straight line obtained from the comonomer content distribution profile is defined by the following formula:

$$\{C(Mc^1)-C(Mc^2)\}/(\log Mc^1-\log Mc^2)$$

wherein:
  $Mc^1$ and $Mc^2$ are two different arbitrary points (Mc) in molecular weight which satisfy the formula (II), and $C(Mc^1)$ and $C(Mc^2)$ are, respectively, comonomer contents corresponding to $Mc^1$ and $Mc^2$ on the approximate straight line.

The comonomer content distribution profile indicates the comonomer contents of copolymer fractions of various molecular weights, and the gradient of the approximate straight line obtained from the profile by the least squares method indicates the change in comonomer content, relative to the change in molecular weight of the copolymer fraction.

With respect to the ethylene copolymers produced using a conventional Ziegler catalyst, the above-mentioned gradient of the approximate straight line has a negative value. This indicates that such conventional ethylene copolymers have a comonomer content distribution such that the higher the molecular weight of a copolymer fraction, the lower the comonomer content of the copolymer fraction.

Even in the case of ethylene copolymers produced using conventional metallocene catalysts which have recently been being put into practical use, the above-mentioned gradient of approximate straight line obtained from the comonomer content distribution profile by the least squares method is almost 0. Even if the errors in measurement are considered, the gradient is smaller than 0.0001.

On the other hand, the ethylene copolymer of the present invention has the above-mentioned gradient [$\{C(Mc^1)-C(Mc^2)\}/(\log Mc^1-\log Mc^2)$] of 0.0005 or more, within the above-defined range in molecular weight of the ethylene copolymer.

This clearly indicates that the ethylene copolymer of the present invention has a specific comonomer content distribution such that, in one aspect, the lower the molecular weight of a copolymer fraction, the lower the comonomer content of the copolymer fraction; and, in the other aspect, the higher the molecular weight of a copolymer fraction, the higher the comonomer content of the copolymer fraction. Due to such a specific comonomer content distribution, the ethylene copolymer of the present invention exhibits various excellent properties, such as high impact strength and excellent ESCR properties, as compared to the conventional ethylene copolymers.

In the present invention, it is preferred that, within the above-defined range in molecular weight of the ethylene copolymer, the above-mentioned gradient be within the range defined by the formula (IV):

$$00.001 \leq \{C(Mc^1)-C(Mc^2)\}/(\log Mc^1-\log Mc^2) \leq 0.02 \qquad \text{(IV)}$$

wherein $Mc^1$, $Mc^2$, $C(Mc^1)$ and $C(Mc^2)$ are as defined for the formula (III).

In the present invention, there is provided a process for obtaining a novel ethylene copolymer.

Specifically, the process comprises copolymerizing ethylene with at least one comonomer selected from the group consisting of a compound represented by the formula $H_2C=CHR$ wherein R is a $C_1$-$C_{20}$ linear, branched or cyclic alkyl group or a $C_6$-$C_{20}$ aryl group, and a $C_4$-$C_{20}$ linear, branched or cyclic diene by slurry polymerization in the presence of a solid catalyst system comprising:
  a support, a transition metal compound, and an activator capable of converting the transition metal compound into a catalytically active transition metal complex.

The reasons for obtaining the unexpected and surprising copolymer properties with the process of the present invention are believed to be as follows.

As already mentioned above, the ethylene copolymer of the present invention has a specific comonomer content distribution such that, in one aspect, the lower the molecular weight of a copolymer fraction, the lower the comonomer content of the copolymer fraction; and, in the other aspect, the higher the molecular weight of a copolymer fraction, the higher the comonomer content of the copolymer fraction.

In addition, for producing the ethylene copolymer of the present invention, the following requirements have to be satisfied:
(i) the produced polymer must not be melted in the reaction mixture but maintains the solid state;
(ii) the polymerization rate at the active species of the catalyst is satisfactorily high; and
(iii) the active species of the catalyst is strongly associated with a carrier, so that the active species of the catalyst is not liberated from the carrier and does not escape from the polymer being produced.

Further, the larger the particle size of a polymer being produced, the easier it becomes to achieve a comonomer content distribution characteristic of the ethylene copolymer of the present invention, namely, a specific comonomer content distribution such that, in one aspect, the lower the molecular weight of a copolymer fraction, the lower the comonomer content of the copolymer fraction; and, in the other aspect, the higher the molecular weight of a copolymer fraction, the higher the comonomer content of the copolymer fraction.

In the method of the present invention for producing an ethylene copolymer, the above-mentioned requirements are satisfied, so that the polymerization reaction can proceed as is explained below.

First, in the method of the present invention, the polymerization reaction is conducted by slurry polymerization, so that the produced polymer is not melted, but maintains the solid state, during the reaction. Therefore, requirement (i) is satisfied.

Second, the preferred catalyst systems to be used in the present invention contain a transition metal compound, i.e., a compound of a transition metal of a Group selected from Groups 3 to 5 of the Periodic Table, wherein the compound contains at least one, preferably only one cyclic π-bonded anionic ligand. Such preferred transition metal compounds, having only one cyclic π-bonded anionic ligand, have a large space around the transition metal, as compared to the space around the transition metal of a metallocene catalyst which contains two or more cyclic or non-cyclic π-bonded anionic ligands. Therefore, with respect to a transition metal compound having only one cyclic or non-cyclic π-bonded anionic ligand, the access of a bulky comonomer to the transition metal is not inhibited, thus enabling the reaction to proceed smoothly. In addition, the preferred catalyst system to be used in the method of the present invention contains a solid component which serves to achieve a high polymerization rate. Therefore, with the catalyst system to be used in the present invention, the rate of polymerization at the active species of the catalyst is satisfactorily high. Hence, the method of the present invention satisfies requirement (ii) above.

Third, in the preferred catalyst systems to be used in the present invention, the active species of the catalyst is strongly associated with a carrier, so that the active species of the catalyst is not liberated from the carrier and does not escape from the polymer being produced.

Specifically stated, in one preferred supported catalyst component to be used in the process of the present invention, the active hydrogen moiety of the activator compound may be bonded to the hydroxyl groups of the support material through an organometal compound. That is, the activator compound is strongly bonded to and carried on the support material. In a further preferred supported catalyst component to be used in the present invention, alumoxane is fixed to the support material by a heating and/or washing treatment, such that the alumoxane is substantially not extractable under severe conditions (toluene at 90° C.). Therefore, requirement (iii) above is met.

The ethylene copolymer of the present invention can be advantageously produced by the method of the present invention using the catalyst system described above, and the catalytic system is especially effective when a catalyst has a relatively large particle size and when the bulk of the comonomer is relatively large.

As described above, the production of the ethylene copolymer of the present invention is enabled only when all of the above-mentioned requirements are simultaneously satisfied. The present inventors have for the first time unexpectedly found the above-mentioned requirements for the production of the excellent ethylene copolymer of the present invention.

Hereinbelow, the method for producing the ethylene copolymer of the present invention will be explained in more detail.

The ethylene copolymer of the present invention is advantageously produced by copolymerizing ethylene with a comonomer using a specific solid catalyst.

Suitable support materials for use in the present invention include porous resinous materials, for example, polyolefins such as polyethylenes and polypropylenes or copolymers of styrene-divinylbenzene, and solid inorganic oxides including oxides of Group 2, 3, 4, 13, or 14 metals, such as silica, alumina, magnesium oxide, titanium oxide, thorium oxide, as well as mixed oxides of silica. Suitable mixed oxides of silica include those of silica and one or more Group 2 or 13 metal oxides, such as silica-magnesia or silica-alumina mixed oxides. Silica, alumina, and mixed oxides of silica and one or more Group 2 or 13 metal oxides are preferred support materials. Preferred examples of such mixed oxides are the silica-aluminas. The most preferred support material is silica. The shape of the silica particles is not critical and the silica may be in granular, spherical, agglomerated, fumed or other form. Suitable silicas include those that are available from Grace Davison (division of W.R. Grace & Co.) under the designations SD 3216.30, SP-9-10046, Davison Syloid™ 245, Davison 948 and Davison 952, from Degussa AG under the designation Aerosil™ 812, and from Crossfield under the designation ES 70X.

Support materials suitable for the present invention preferably have a surface area as determined by nitrogen porosimetry using the B.E.T. method from 10 to about 1000 m²/g, and preferably from about 100 to 600 m²/g. The pore volume of the support, as determined by nitrogen adsorption, is typically up to 5 cm³/g, advantageously between 0.1 and 3 cm³/g, preferably from about 0.2 to 2 cm³/g. The average particle size is not critical but typically is from 0.5 to 500 μm, preferably from 1 to 200 μm, more preferably to 100 μm.

The support material may be subjected to a heat treatment and/or chemical treatment to reduce the water content or the hydroxyl content of the support material. Both dehydrated support materials and support materials containing small amounts of water can be used. Typical thermal pretreatments are carried out at a temperature from 30° C. to 1000° C. for a duration of 10 minutes to 50 hours in an inert atmosphere or under reduced pressure. Typical support materials have a surface hydroxyl content of from 0.1 micromol, preferably from 5 micromol, more preferably from 0.05 mmol to not more than 10 mmol and preferably not more than 5 mmol hydroxyl groups per g of solid support, more preferably from 0.5 to 2 mmol per gram. The hydroxyl content can be determined by known techniques, such as infrared spectroscopy and titration techniques using a metal alkyl or metal hydroxide, for example, adding an excess of dialkyl magnesium to a slurry of the solid support and determining the amount of dialkyl magnesium remaining in solution via known techniques. This latter method is based on the reaction of S—OH+MgR$_2$→S—OMgR+RH, wherein S is the solid support.

As an alternative technique for measuring the amount of hydroxyl groups on the surface of the inorganic solid, a method comprising the following procedures can be utilized. Illustratively stated, the inorganic solid is dried in a nitrogen gas flow at 250° C. for 10 hours and then, the weight of the dried inorganic solid is measured and taken as an initial weight represented by "W1" (unit: g). After this, the dried inorganic solid is heated to 1,000° C. and then, allowed to cool to the room temperature. The weight of the cooled inorganic solid is measured, and the difference between the initial weight (W1) and the weight of the cooled inorganic solid is determined and taken as a weight loss represented by "ΔW" (unit: g). The amount of the hydroxyl groups is calculated by the following formula:

Amount of the hydroxyl groups=(1,000×ΔW/18.02)/W1 mmol/g     (V).

It is preferred that the inorganic solid having hydroxyl groups on the surface thereof to be used in the method of the present invention does not contain water such as crystal water or adsorbed water.

Any water contained in the inorganic solid can be removed therefrom by heating in a nitrogen atmosphere or under reduced pressure at 250° C. or more for 1 hour or more.

Suitable transition metal compounds for use in the present invention are those that can be converted by an activator compound (b) to thereby form a catalytically active transition metal complex. The transition metal compounds may be derivatives of any transition metal including Lanthanides, preferably from Groups 3, 4, 5, and 6, more preferably the Group 3 or 4 transition metals or the Lanthanides, which transition metals are in the +2, +3, or +4 formal oxidation state. The transition metals preferably contain at least one π-anionic ligand group which can be a cyclic or noncyclic delocalized π-bonded anionic ligand group. Exemplary of such π-bonded anionic ligand groups are conjugated or non-conjugated, cyclic or non-cyclic dienyl groups, allyl groups, aryl groups, as well as substituted derivatives of such groups.

The term "derivative" when used to describe the above-substituted, delocalized π-bonded groups means that each atom in the delocalized π-bonded group may independently be substituted with a radical selected from the group consisting of halogen, hydrocarbyl, halohydrocarbyl, and hydrocarbyl-substituted metalloid radicals wherein the metalloid is selected from Group 14 of the Periodic Table of the Elements. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system or a hydrogenated fused ring system. Suitable hydrocarbyl-substituted organo-metalloid radicals include mono-, di- and tri-substituted organo-metalloid radicals of Group 14 elements wherein each of the hydrocarbyl groups contains from 1 to 20 carbon atoms. More particularly, suitable hydrocarbyl-substituted organo-metalloid radicals include trimethylsilyl, triethylsilyl, ethyldimethylsilyl, methyldiethylsilyl, triphenylgermyl, trimethylgermyl and the like.

Preferred anionic, delocalized π-bonded groups include cyclopentadienyl and substituted cyclopentadienyl groups. Especially preferred are cyclopentadienyl, indenyl, fluorenyl, tetrahydroindenyl, tetrahydrofluorenyl, and octahydrofluorenyl. Other examples of preferred anionic ligand groups are pentadienyl, cyclohexa dienyl, dihydroanthracenyl, hexahydroanthracenyl, and decahydroanthracenyl groups, and methyl-substituted derivatives thereof.

Suitable transition metal compounds (c) may be a cyclopentadienyl or substituted cyclopentadienyl derivative of any transition metal including Lanthanides, but preferably of the Group 3, 4, or Lanthanide transition metals. Suitable transition metal compounds for use in the present invention are the bridged or unbridged mono-, bis-, and tri-cyclopentadienyl or substituted cyclopentadienyl transition metal compounds. Suitable unbridged monocyclopentadienyl or mono(substituted cyclopentadienyl) transition metal derivatives are represented by the following formula (VI):

$$CpMX_n \qquad (VI)$$

wherein Cp is cyclopentadienyl or a derivative thereof, M is a Group 3, 4, or 5 transition metal having a formal oxidation state of +2, +3 or +4, X independently in each occurrence represents an anionic ligand group (other than a cyclic, aromatic π-bonded anionic ligand group) selected from the group of hydrocarbyl, hydrocarbylene (including hydrocarbadienyl), hydrocarbyloxy, hydride, halo, silyl, germyl, amide, and siloxy radicals having up to 50 nonhydrogen atoms, and n, a number equal to one less than the formal oxidation state of M, is 1, 2 or 3, preferably 3. Preferably, at least one of X is a hydrocarbyl radical having from 1 to about 20 carbon atoms, a substituted-hydrocarbyl radical having from 1 to about 20 carbon atoms wherein one or more of the hydrogen atoms are replaced with a halogen atom, or an organo-metalloid radical comprising a Group 14 element wherein each of the hydrocarbyl substituents contained in the organo portion of said organo-metalloid, independently, contain from 1 to about 20 carbon atoms.

Suitable bridged monocyclopentadienyl or mono(substituted cyclopentadienyl) transition metal compounds include the so-called constrained geometry complexes. Examples of such complexes and methods for their preparation are disclosed in U.S. application Ser. No. 545,403, filed Jul. 3, 1990 now abandoned, (corresponding to EP-A-416,815), U.S. application Ser. No. 241,523, filed May 12, 1994, now U.S. Pat. No. 5,470,993, (corresponding to WO-95/00526), as well as U.S. Pat. Nos. 5,055,438, 5,057,475, 5,096,867, 5,064,802 5,132,380, and 5,374,696 all of which are incorporated herein by reference.

More particularly, preferred bridged monocyclopentadienyl or mono(substituted cyclopentadienyl) transition metal compounds correspond to the following formula (VII):

(VII)

wherein:
M is a metal of Group 3-5, especially a Group 4 metal, particularly titanium;
Cp* is a substituted cyclopentadienyl group bound to Z' and, in an $\eta^5$ bonding mode, to M or such a group is further substituted with from one to four substituents selected from the group consisting of hydrocarbyl, silyl, germyl, halo, hydrocarbyloxy, amine, and mixtures thereof, said substituent having up to 20 nonhydrogen atoms, or optionally, two such further substituents together cause Cp* to have a fused ring structure;
Z' is a divalent moiety other than a cyclic or noncyclic π-bonded anionic ligand, said Z' comprising boron, or a member of Group 14 of the Periodic Table of the Elements, and optionally nitrogen, phosphorus, sulfur or oxygen, said moiety having up to 20 non-hydrogen atoms, and optionally Cp* and Z' together form a fused ring system;
X independently each occurrence represents an anionic ligand group (other than a cyclic, aromatic π-bonded anionic ligand group) selected from the group of hydrocarbyl, hydrocarbylene (including hydrocarbadienyl), hydrocarbyloxy, hydride, halo, silyl, germyl, amide, and siloxy radicals having up to 50 nonhydrogen atoms, preferably X is selected from the group of a hydride radical, hydrocarbyl radical, substituted-hydrocarbyl radical, or organo-metalloid radical; and n is 1 or 2 depending on the valence of M.

In consonance with the previous explanation, M is preferably a Group 4 metal, especially titanium; n is 1 or 2; and X is monovalent ligand group of up to 30 nonhydrogen atoms, more preferably, $C_{1-20}$ hydrocarbyl.

When n is 1 and the Group 3-5 metal (preferably the Group 4 metal) is in the +3 formal oxidation state, X is preferably a stabilizing ligand.

By the term "stabilizing ligand" is meant that the ligand group stabilizes the metal complex through either:
1) a nitrogen, phosphorus, oxygen or sulfur chelating bond, or
2) an $\eta^3$ bond with a resonant, delocalized π-electronic structure.

Examples of stabilizing ligands of group 1) include silyl, hydrocarbyl, amido or phosphido ligands substituted with one or more aliphatic or aromatic ether, thioether, amine or phosphine functional groups, especially such amine or phosphine groups that are tertiary-substituted, said stabilizing ligand having from 3 to 30 nonhydrogen atoms. Most preferred group 1) stabilizing ligands are 2-dialkylaminobenzyl or 2-(dialkylaminomethyl)-phenyl groups containing from 1 to 4 carbons in the alkyl groups.

Examples of stabilizing ligands of group 2) include $C_{3-10}$ hydrocarbyl groups containing ethylenic unsaturation, such as allyl, 1-methylallyl, 2-methylallyl, 1,1-dimethylallyl, or 1,2,3-trimethylallyl groups.

More preferably still, such metal coordination complexes correspond to the following formula (VIII):

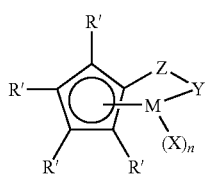

(VIII)

wherein R' in each occurrence is independently selected from the group consisting of hydrogen, hydrocarbyl, silyl, germyl, cyano, halo and combinations thereof having up to 20 nonhydrogen atoms, or two R' groups together form a divalent derivative thereof;

X has the same meaning as defined for formula (VI);

Y is a divalent anionic ligand group comprising nitrogen, phosphorus, oxygen or sulfur and having up to 20 nonhydrogen atoms, said Y being bonded to Z and M through said nitrogen, phosphorus, oxygen or sulfur, and optionally Y and Z together form a fused ring system;

M is a Group 4 metal, especially titanium;

Z is $SiR*_2$, $CR*_2$, $SiR*_2SiR*_2$, $CR*_2CR*_2$, $CR*=CR*$, $CR*_2SiR*_2$, $GeR*_2$, $BR*$, or $BR*_2$; wherein:

R* in each occurrence is independently selected from the group consisting of hydrogen, hydrocarbyl, silyl, halogenated alkyl, halogenated aryl groups having up to 20 non-hydrogen atoms, and mixtures thereof, or two or more R* groups from Z, or an R* group from Z together with Y form a fused ring system; and n is 1 or 2.

Further more preferably, Y is —O—, —S—, —NR*—, —PR*—. Highly preferably Y is a nitrogen or phosphorus containing group corresponding to the formula —N(R')— or —P(R')—, wherein R' is as previously described, i.e., an amido or phosphido group.

Most highly preferred metal coordination complexes correspond to the following formula (IX):

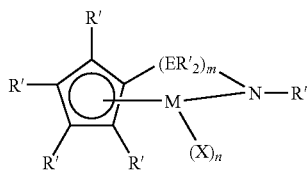

(IX)

wherein:

M is titanium;

R' each occurrence is independently selected from the group consisting of hydrogen, silyl, hydrocarbyl and combinations thereof having up to 10 carbon or silicon atoms, or two R' groups of the substituted cyclopentadienyl moiety are joined together;

E is silicon or carbon;

X independently each occurrence is hydride, alkyl, aryl, of up to 10 carbons;

m is 1 or 2; and n is 1 or 2.

Examples of the above most highly preferred metal coordination compounds include compounds wherein the R' on the amido group is methyl, ethyl, propyl, butyl, pentyl, hexyl, (including isomers), norbornyl, benzyl, phenyl, and cyclododecyl; $(ER'2)_m$ is dimethyl silane or 1,2-ethylene; R' on the cyclic π-bonded group independently each occurrence is hydrogen, methyl, ethyl, propyl, butyl, pentyl, hexyl, norbornyl, benzyl, and phenyl, or two R' groups are joined forming an indenyl, tetrahydroindenyl, fluorenyl or octahydrofluorenyl moiety; and X is methyl, ethyl, propyl, butyl, pentyl, hexyl, norbornyl, benzyl, and phenyl.

Transition metal compounds wherein the transition metal is in the +2 formal oxidation state include those complexes containing one and only one cyclic, delocalized, anionic, π-bonded group, said complexes corresponding to the following formula (X):

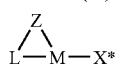

(X)

wherein:

M is titanium or zirconium in the +2 formal oxidation state;

L is a group containing a cyclic, delocalized, anionic, π-system through which the group is bonded to M, and which group is also bonded to Z;

Z is a moiety bonded to M via a π-bond, comprising boron, or a member of Group 14 of the Periodic Table of the Elements, and also comprising nitrogen, phosphorus, sulfur or oxygen, said moiety having up to 60 non-hydrogen atoms; and X* is a neutral, conjugated or nonconjugated diene, optionally substituted with one or more hydrocarbyl groups, said X having up to 40 carbon atoms and forming a π-complex with M.

Preferred transition metal compounds of formula (X) include those wherein Z, M and X* are as previously defined; and L is a $C_5H_4$ group bonded to Z and bound in an $\eta^5$ bonding mode to M or is such an $\eta^5$ bound group substituted with from one to four substituents independently selected from hydrocarbyl, silyl, germyl, halo, cyano, and combinations thereof, said substituent having up to 20 nonhydrogen atoms, and optionally, two such substituents (except cyano or halo) together cause a fused ring structure.

More preferred transition metal +2 compounds according to the present invention correspond to the following formula (XI)):

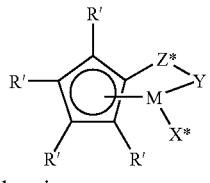

(XI)

wherein:

R' in each occurrence is independently selected from hydrogen, hydrocarbyl, silyl, germyl, halo, cyano, and combinations thereof, said R' having up to 20 nonhydrogen atoms, and optionally, two R' groups (where R' is not hydrogen, halo or cyano) together form a divalent derivative thereof connected to adjacent positions of the cyclopentadienyl ring to form a fused ring structure;

X* is a neutral $\eta^4$-bonded diene group having up to 30 nonhydrogen atoms, which forms a π-complex with M;

Y is —O—, —S—, —NR*13 , —PR*—;

M is titanium or zirconium in the +2 formal oxidation state;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$; wherein:

R* each occurrence is independently hydrogen, or a member selected from hydrocarbyl, silyl, halogenated alkyl, halogenated aryl, and combinations thereof, said R* having up to 10 nonhydrogen atoms, and optionally, two R* groups from Z* (when R* is not hydrogen), or an R* group from Z* and an R* group from Y form a ring system.

Preferably, R' independently each occurrence is hydrogen, hydrocarbyl, silyl, halo and combinations thereof said R' having up to 10 nonhydrogen atoms, or two R' groups (when R' is not hydrogen or halo) together form a divalent derivative thereof; most preferably, R' is hydrogen, methyl, ethyl, propyl, butyl, pentyl, hexyl, (including where appropriate all isomers), cyclopentyl, cyclohexyl, norbornyl, benzyl, or phenyl or two R' groups (except hydrogen) are linked together, the entire $C_5R'_4$ group thereby being, for example, an indenyl, tetrahydroindenyl, fluorenyl, tetrahydrofluorenyl, or octahydrofluorenyl group.

Further preferably, at least one of R' or R* is an electron donating moiety. By the term "electron donating" is meant that the moiety is more electron donating than hydrogen. Thus, highly preferably Y is a nitrogen or phosphorus containing group corresponding to the formula —N(R")— or —P(R")—, wherein R" is $C_{1-10}$ hydrocarbyl.

Examples of suitable X* groups include: s-trans-$\eta^4$-1,4-diphenyl-1,3-butadiene; s-trans-$\eta^4$-3-methyl-1,3-pentadiene; s-trans-$\eta^4$-1,4-dibenzyl-1,3-butadiene; s-trans-$\eta^4$-2,4-hexadiene; s-trans-$\eta^4$-1,3-pentadiene; s-trans-$\eta^4$-1,4-ditolyl-1,3-butadiene; s-trans-$\eta^4$-1,4-bis(trimethylsilyl)-1,3-butadiene; s-cis-$\eta^4$-1,4-diphenyl-1,3-butadiene; s-cis-$\eta^4$-3-methyl-1,3-pentadiene; s-cis-$\eta^4$-1,4-dibenzyl-1,3-butadiene; s-cis-$\eta^4$-2,4-hexadiene; s-cis-$\eta^4$-1,3-pentadiene; s-cis-$\eta^4$-1,4-ditolyl-1,3-butadiene; and s-cis-$\eta^4$-1,4-bis(trimethylsilyl)-1,3-butadiene, said s-cis diene group forming a π-complex as defined herein with the metal.

Most highly preferred transition metal +2 compounds are amidosilane- or amidoalkanediyl-compounds of formula (XI) wherein:

-Z*-Y— is —$(ER'''^2)_m$—N(R")—, and R' each occurrence is independently selected from hydrogen, silyl, hydrocarbyl and combinations thereof, said R' having up to 10 carbon or silicon atoms, or two such R' groups on the substituted cyclopentadienyl group (when R' is not hydrogen) together form a divalent derivative thereof connected to adjacent positions of the cyclopentadienyl ring;

R" is $C_{1-10}$ hydrocarbyl;

R''' is independently each occurrence hydrogen or $C_{1-10}$ hydrocarbyl;

E is independently each occurrence silicon or carbon; and m is 1 or 2.

Examples of the metal complexes according to the present invention include compounds wherein R" is methyl, ethyl, propyl, butyl, pentyl, hexyl, (including all isomers of the foregoing where applicable), cyclododecyl, norbornyl, benzyl, or phenyl; $(ER'''_2)_m$ is dimethylsilane, or ethanediyl; and the cyclic delocalized π-bonded group is cyclopentadienyl, tetramethylcyclopentadienyl, indenyl, tetrahydroindenyl, fluorenyl, tetrahydrofluorenyl or octahydrofluorenyl.

Suitable bis(cyclopentadienyl) derivatives of transition metals include those of titanium, zirconium and hafnium compounds and may be represented by the following general formulae (XII) to (XV):

$(A-Cp)MX_1X_2$           (XII)

$(A-Cp)MX'_1X'_2$          (XIII)

$(A-Cp)ML$              (XIV)

$(Cp^*)(CpR)MX_1$          (XV)

wherein: M is a Group 4 metal namely titanium (Ti), zirconium (Zr) and hafnium (Hf); (A-Cp) is either (Cp)(Cp*) or Cp-A'-Cp* and Cp and Cp* are the same or different cyclopentadienyl radicals, as well as substituted derivatives of cyclopentadienyl radicals, and A' is a covalent bridging group containing a Group 14 element; L is an olefin, diolefin or aryne ligand; at least one of $X_1$ and $X_2$ is a hydride radical, hydrocarbyl radical, substituted-hydrocarbyl radical, or organo-metalloid radical, the other of $X_1$ and $X_2$ being a hydride radical, hydrocarbyl radical, substituted-hydrocarbyl radical, organo-metalloid radical, or a hydrocarbyloxy radical; preferably one or both of $X_1$ and $X_2$ is a hydrocarbyl radical having from 1 to about 20 carbon atoms, substituted-hydrocarbyl radical having from 1 to about 20 carbon atoms wherein one or more of the hydrogen atoms are replaced with a halogen atom, organo-metalloid radical comprising a Group 14 element wherein each of the hydrocarbyl substituents contained in the organo portion of said organo-metalloid, independently, contain from 1 to about 20 carbon atoms; $X'_1$ and $X'_2$ are joined and bound to the metal atom to form a metallacycle, in which the metal, $X'_1$ and $X'_2$ form a hydrocarbocyclic ring containing from about 3 to about 20 carbon atoms; and R is a substituent, preferably a hydrocarbyl substituent, having from 1 to 20 carbon atoms on one of the cyclopentadienyl radicals, which is also bound to the metal atom.

When not both $X_1$ and $X_2$ are a hydride radical, hydrocarbyl radical, substituted-hydrocarbyl radical, or organo-metalloid radical one of these can be a hydrocarbyloxy radical having from 1 to 20 carbon atoms. Suitable examples of hydrocarbyloxy radicals include alkyloxy, aryloxy, aralkyloxy, and alkaryloxy radicals having from 1 to 20 carbon atoms, more preferably alkyl radicals having from 1 to 6 carbon atoms, and aryl, aralkyl and alkaryl radicals having from 6 to 10 carbon atoms, even more preferably isopropyloxy, n-butyloxy, or t-butyloxy.

Examples of such bis(cyclopentadienyl) derivatives of transition metals and methods for their preparation are disclosed in U.S. Pat. No. 5,384,299 (corresponding to EP-A-277,004) and U.S. application Ser. No. 459,921, filed Jan. 2, 1990, now abandoned, (corresponding to WO-91/09882), which are incorporated herein by reference.

Suitable tri-cyclopentadienyl or substituted cyclopentadienyl transition metal compounds include those containing a bridging group linking two cyclopentadienyl groups and those without such bridging groups.

Suitable unbridged tri-cyclopentadienyl transition metal derivatives are represented by the following formula (XVI):

$CP_3MX_n''$           (XVI)

wherein Cp, M and X are as defined for formula (VI) and n" is three less than the formal oxidation state of M and is 0 or 1, preferably 1. Preferred ligand groups X are hydrocarbyl, hydrocarbyloxy, hydride, halo, silyl, germyl, amide, and siloxy.

According to one preferred embodiment, the solid (or supported) catalyst comprises:

a supported catalyst component comprising (a) a support material, and an organometal compound wherein the metal is selected from Groups 2-13 of the Periodic Table of the Elements, germanium, tin, and lead, and (b) an activator compound comprising (b-1) a cation which is capable of reacting with a transition metal compound to form a catalytically active transition metal complex, and (b-2) a compatible anion having up to 100 nonhydrogen atoms and containing at least one substituent comprising an active hydrogen moiety; and a transition metal compound.

The support material is typically treated with the organometal compound. Suitable organometal compounds are those comprising metals of Groups 2-13, germanium, tin, and lead, and at least two substituents selected from hydride, hydrocarbyl radicals, trihydrocarbyl silyl radicals, and trihydrocarbyl germyl radicals. Additional substituents preferably comprise one or more substituents selected from hydride, hydrocarbyl radicals, trihydrocarbyl substituted silyl radicals, trihydrocarbyl substituted germyl radicals, and hydrocarbyl-, trihydrocarbyl silyl- or trihydrocarbyl germyl-substituted metalloid radicals.

The recitation "metalloid", as used herein, includes nonmetals such as boron, phosphorus and the like which exhibit semi-metallic characteristics.

Examples of such organometal compounds include organomagnesium, organozinc, organoboron, organoaluminum, organogermanium, organotin, and organolead compounds, and mixtures thereof. Further suitable organometal compounds are alumoxanes. Preferred examples are alumoxanes and compounds represented by the following formulae: $MgR^1_2$, $ZnR^1_2$, $BR^1_xR^2_y$, $AlR^1_xR^2_y$, wherein $R^1$ independently each occurrence is hydride, a hydrocarbyl radical, a trihydrocarbyl silyl radical, a trihydrocarbyl germyl radical, or a trihydrocarbyl-, trihydrocarbyl silyl-, or trihydrocarbyl germyl-substituted metalloid radical, $R^2$ independently is the same as $R_1$, x is 2 or 3, y is 0 or 1 and the sum of x and y is 3, and mixtures thereof. Examples of suitable hydrocarbyl moieties are those having from 1 to 20 carbon atoms in the hydrocarbyl portion thereof, such as alkyl, aryl, alkaryl, or aralkyl. Preferred radicals include methyl, ethyl, n- or i-propyl, n-, s- or t-butyl, phenyl, and benzyl. Preferably, the aluminum component is selected from the group consisting of alumoxane and aluminum compounds of the formula $AlR^1_x$ wherein $R^1$ in each occurrence independently is hydride or a hydrocarbyl radical having from 1 to 20 carbon atoms, and x is 3. Suitable trihydrocarbyl aluminum compounds are trialkyl or triaryl aluminum compounds wherein each alkyl or aryl group has from 1 to 10 carbon atoms, or mixtures thereof, and preferably trialkyl aluminum compounds such as trimethyl, triethyl, triisobutyl aluminum.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (—Al(R)—O—)$_m$, for a cyclic alumoxane, and $R_2Al$—O(—Al(R)—O—)$_m$—$AlR_2$, for a linear compound, wherein R independently in each occurrence is a $C_1$-$C_{10}$ hydrocarbyl, preferably alkyl, or halide and m is an integer ranging from 1 to about 50, preferably at least about 4. Alumoxanes are typically the reaction products of water and an aluminum alkyl, which in addition to an alkyl group may contain halide or alkoxide groups. Reacting several different aluminum alkyl compounds, such as, for example, trimethyl aluminum and triisobutyl aluminum, with water yields so-called modified or mixed alumoxanes. Preferred alumoxanes are methylalumoxane and methylalumoxane modified with minor amounts of other lower alkyl groups such as isobutyl. Alumoxanes generally contain minor to substantial amounts of starting aluminum alkyl compound.

The way in which the alumoxane is prepared is not critical. When prepared by the reaction between water and aluminum alkyl, the water may be combined with the aluminum alkyl in various forms, such as liquid, vapor, or solid, for example in the form of crystallization water. Particular techniques for the preparation of alumoxane type compounds by contacting an aluminum alkyl compound with an inorganic salt containing water of crystallization are disclosed in U.S. Pat. No. 4,542,199. In a particular preferred embodiment an aluminum alkyl compound is contacted with a regeneratable water-containing substance such as hydrated alumina, silica or other substance. This is disclosed in European Patent Application No. 338,044.

The supported catalyst according to this embodiment generally comprises a support material combined or treated with the organometal compound and containing at least 0.1 micromol of organometal compound per g of support material, typically at least 5 micromole per g support material, advantageously at least 0.5 weight percent of the metal, preferably aluminum, expressed in gram of metal atoms per g of support material. Preferably, the amount of metal is at least 2 weight percent, and generally not more than 40 weight percent, and more preferably not more than 30 weight percent. At too high amounts of metal the supported catalyst becomes expensive. At too low amounts the catalyst efficiency goes down to drop below acceptable levels.

The supported catalysts preferably contains a treated support material (a) comprising a support material and an alumoxane wherein not more than about 10 percent aluminum present in the treated support material is extractable in a one hour extraction with toluene of 90° C. using about 10 mL toluene per gram of pretreated support material. More preferably, not more than about 9 percent aluminum present in the supported catalyst component is extractable, and most preferably not more than about 8 percent. This is especially advantageous when the supported catalyst is used in a polymerization process where a diluent or solvent is used which may extract non-fixed alumoxane from the support material. It has been found that when the amount of extractables is below the levels given above, the amount of alumoxane that can diffuse into the polymerization solvent or diluent, if used, is so low that no appreciable amount of polymer will be formed in the diluent, as compared to polymer formed on the support material. If too much polymer is formed in the diluent the polymer bulk density will decrease below acceptable levels and reactor fouling problems may occur.

The toluene extraction test is carried out as follows: About 1 g of supported catalyst component or supported catalyst, with a known aluminum content, is added to 10 mL toluene and the mixture is then heated to 90° C. under an inert atmosphere. The suspension is stirred well at this temperature for 1 hour. Then the suspension is filtered applying reduced pressure to assist in the filtration step. The solids are washed twice with about 3 to 5 mL toluene of 90° C. per gram of solids. The solids are then dried at 120° C. for 1 hour, and subsequently the aluminum content of the solids is measured. The difference between the initial aluminum content and the aluminum content after the extraction divided by the initial aluminum content and multiplied by 100%, gives the amount of extractable aluminum.

The aluminum content can be determined by slurrying about 0.5 g of supported catalyst component or supported catalyst in 10 mL hexane. The slurry is treated with 10 to 15 mL 6N sulfuric acid, followed by addition of a known excess of EDTA. The excess amount of EDTA is then back-titrated with zinc chloride.

Without wishing to be bound by any theory, it is believed that the activator compound according to this embodiment reacts with the organometal compound through the active hydrogen-containing substituent. It is believed that a group $R^1$ of the organometal compound combines with the active hydrogen moiety of the activator compound to release a neutral organic compound, for example an alkane, or hydrogen gas thereby chemically coupling the metal atom with the activator compound residue. Thus the activator is believed to become chemically attached to the support material once the support material has been treated with the organometal compound or adduct of organometal compound and activator compound. Upon addition of the transition metal compound a supported catalyst is formed having improved properties.

The activator compound useful in the present invention contains a compatible anion having up to 100, and preferably up to 50 nonhydrogen atoms and having at least one substituent comprising an active hydrogen moiety. Preferred substituents comprising an active hydrogen moiety correspond to the formula (XVII):

$$G_q(T-H)_r \qquad (XVII)$$

wherein G is a polyvalent hydrocarbon radical, T is O, S, NR, or PR, wherein R is a hydrocarbyl radical, a trihydrocarbyl silyl radical, a trihydrocarbyl germyl radical, or hydrogen, q is 0 or 1, and preferably 1, and r is an integer from 1 to 3, preferably 1. Polyvalent hydrocarbon radical G has r+1 valencies, one valency being with a metal or metalloid of the Groups 5-15 of the Periodic Table of the Elements in the compatible anion, the other valency or valencies of G being attached to r groups T-H. Preferred examples of G include divalent hydrocarbon radicals such as: alkylene, arylene, aralkylene, or alkarylene radicals containing from 1 to 20 carbon atoms, more preferably from 2 to 12 carbon atoms. Suitable examples of G include phenylene, biphenylene, naphthylene, methylene, ethylene, 1,3-propylene, 1,4-butylene, phenylmethylene (—$C_6H_4$—$CH_2$—). The polyvalent hydrocarbyl portion G may be further substituted with radicals that do not interfere with the coupling function of the active hydrogen moiety. Preferred examples of such non-interfering substituents are alkyl, aryl, alkyl- or aryl-substituted silyl and germyl radicals, and fluoro substituents.

The group T—H in the previous formula thus may be an —OH, —SH, —NRH, or —PRH group, wherein R preferably is a $C_{1-18}$, preferably a $C_{1-10}$ hydrocarbyl radical or hydrogen, and H is hydrogen. Preferred R groups are alkyls, cycloalkyls, aryls, arylalkyls, or alkylaryls of 1 to 18 carbon atoms, more preferably those of 1 to 12 carbon atoms. The —OH, —SH, —NRH, or —PRH groups may be part of a larger functionality such as, for example, C(O)—OH, C(S)—SH, C(O)—NRH, and C(O)—PRH. Most preferably, the group T-H is a hydroxy group, —OH, or an amino group, —NRH.

Very preferred substituents $G_q(T-H)_r$ comprising an active hydrogen moiety include hydroxy- and amino-substituted aryl, aralkyl, alkaryl or alkyl groups, and most preferred are the hydroxyphenyls, especially the 3- and 4-hydroxyphenyl groups, hydroxytolyls, hydroxy benzyls (hydroxymethylphenyl), hydroxybiphenyls, hydroxynaphthyls, hydroxycyclohexyls, hydroxymethyls, and hydroxypropyls, and the corresponding amino-substituted groups, especially those substituted with —NRH wherein R is an alkyl or aryl radical having from 1 to 10 carbon atoms, such as for example methyl, ethyl, propyl, i-propyl, n-, i-, or t-butyl, pentyl, hexyl, heptyl, octyl, nonyl, and decyl, phenyl, benzyl, tolyl, xylyl, naphthyl, and biphenyl.

The compatible anion containing the substituent which contains an active hydrogen moiety, may further comprise a single Group 5-15 element or a plurality of Group 5-15 elements, but is preferably a single coordination complex comprising a charge-bearing metal or metalloid core, which anion is bulky. A compatible anion specifically refers to an anion which when functioning as a charge balancing anion in the catalyst system of this invention, does not transfer an anionic substituent or fragment thereof to the transition metal cation thereby forming a neutral transition metal compound and a neutral metal by-product. "Compatible anions" are anions which are not degraded to neutrality when the initially formed complex decomposes and are noninterfering with desired subsequent polymerizations.

Preferred anions are those containing a single coordination complex comprising a charge-bearing metal or metalloid core carrying a substituent containing an active hydrogen moiety which anion is relatively large (bulky), capable of stabilizing the active catalyst species (the transition metal cation) which is formed when the activator compound and transition metal compound are combined and said anion will be sufficiently labile to be displaced by olefinic, diolefinic and acetylenically unsaturated compounds or other neutral Lewis bases such as ethers, nitrites and the like. Suitable metals for the anions of activator compounds include, but are not limited to, aluminum, gold, platinum and the like. Suitable metalloids include, but are not limited to, boron, phosphorus, silicon and the like. Activator compounds which contain anions comprising a coordination complex containing a single boron atom and a substituent comprising an active hydrogen moiety are preferred.

Preferably, compatible anions containing a substituent comprising an active hydrogen moiety may be represented by the following general formula (XVIII):

$$[M'^{m+}Q_n(G_q(T-H)_r)_z]_{d-} \qquad (XVIII)$$

wherein:
M' is a metal or metalloid selected from Groups 5-15 of the Periodic Table of the Elements;
Q independently in each occurrence is selected from the group consisting of hydride, dihydrocarbylamido, preferably dialkylamido, halide, hydrocarbyloxide, preferably alkoxide and aryloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion having from 1 to 20 carbons with the proviso that in not more than one occurrence is Q halide;
G is a polyvalent, having r+1 valencies and preferably divalent hydrocarbon radical bonded to M' and T;
T is O, S, NR, or PR, wherein R is a hydrocarbon radical, a trihydrocarbyl silyl radical, a trihydrocarbyl germyl radical, or hydrogen;
m is an integer from 1 to 7, preferably 3;
n is an integer from 0 to 7, preferably 3;
q is an integer 0 or 1, preferably 1;
r is an integer from 1 to 3, preferably 1;

z is an integer from 1 to 8, preferably 1;
d is an integer from 1 to 7, preferably 1; and
n+z−m=d.

Preferred boron-containing anions which are particularly useful in this invention may be represented by the following general formula (XIX):

$$[BQ_{4-z'}(G_q(T-H)_r)_{z'}]^{d-} \tag{XIX}$$

wherein:
B is boron in a valence state of 3;
z' is an integer from 1-4, preferably 1;
d is 1; and
Q, G, T, H, q, and r are as defined for formula (XVIII). Preferably, z' is 1, q is 1, and r is 1.

Illustrative, but not limiting, examples of anions of activator compounds to be used in the present invention are boron-containing anions such as triphenyl(hydroxyphenyl)borate, diphenyl-di(hydroxyphenyl)borate, triphenyl(2,4-dihydroxyphenyl)borate, tri(p-tolyl)(hydroxyphenyl)borate, tris(pentafluorophenyl)(hydroxyphenyl)borate, tris-(2,4-dimethylphenyl)(hydroxyphenyl)borate, tris-(3,5-dimethylphenyl)(hydroxyphenyl)borate, tris-(3,5-di-trifluoromethylphenyl)(hydroxyphenyl)borate, tris(pentafluorophenyl)(2-hydroxyethyl)borate, tris(pentafluorophenyl)(4-hydroxybutyl)borate, tris(pentafluorophenyl)(4-hydroxycyclohexyl)borate, tris(pentafluorophenyl)(4-(4'-hydroxyphenyl)phenyl)borate, tris(pentafluorophenyl)(6-hydroxy-2-naphthyl)borate, and the like. A highly preferred activator complex is tris(pentafluorophenyl)(4-hydroxyphenyl)borate. Other preferred anions of activator compounds are those above mentioned borates wherein the hydroxy functionality is replaced by an amino NHR functionality wherein R preferably is methyl, ethyl, or t-butyl.

The cationic portion (b-1) of the activator compound to be used in association with the compatible anion (b-2) can be any cation which is capable of reacting with the transition metal compound to form a catalytically active transition metal complex, especially a cationic transition metal complex. The cations (b-1) and the anions (b-2) are used in such ratios as to give a neutral activator compound. Preferably the cation is selected from the group consisting of Brønsted acidic cations, carbonium cations, silylium cations, and cationic oxidizing agents.

Brønsted acidic cations may be represented by the following general formula:

$$(L-H)^+$$

wherein:
L is a neutral Lewis base, preferably a nitrogen, phosphorus, or sulfur containing Lewis base; and (L-H)$^+$ is a Brønsted acid. The Brønsted acidic cations are believed to react with the transition metal compound by transfer of a proton of said cation, which proton combines with one of the ligands on the transition metal compound to release a neutral compound.

Illustrative, but not limiting, examples of Brønsted acidic cations of activator compounds to be used in the present invention are trialkyl-substituted ammonium cations such as triethylammonium, tripropylammonium, tri(n-butyl)ammonium, trimethylammonium, tributylammonium, and tri(n-octyl)ammonium. Also suitable are N,N-dialkyl anilinium cations such as N,N-dimethylanilinium, N,N-diethylanilinium, N,N-2,4,6-pentamethylanilinium, N,N-dimethylbenzylammonium and the like; dialkylammonium cations such as di-(i-propyl)ammonium, dicyclohexylammonium and the like; and triarylphosphonium cations such as triphenylphosphonium, tri(methylphenyl)phosphonium, tri(dimethylphenyl)phosphonium, dimethylsulphonium, diethylsulphonium, and diphenylsulphonium.

A second type of suitable cation corresponds to the formula:

$$\text{C}^+$$

wherein $\text{C}^+$ is a stable carbonium or silylium ion containing up to 30 nonhydrogen atoms, the cation being capable of reacting with a substituent of the transition metal compound and converting it into a catalytically active transition metal complex, especially a cationic transition metal complex. Suitable examples of cations include tropyllium, triphenylmethylium, benzene(diazonium). Silylium salts have been previously generically disclosed in J. Chem. Soc. Chem. Comm., 1993, 383-384, as well as Lambert, J. B., et. al., Organometallics, 1994, 13, 2430-2443. Preferred silylium cations are triethylsilylium, and trimethylsilylium and ether substituted adducts thereof.

Another suitable type of cation comprises a cationic oxidizing agent represented by the formula:

$$Ox^{e+}$$

wherein $Ox^{e+}$ is a cationic oxidizing agent having a charge of e+, and e is an integer from 1 to 3.

Examples of cationic oxidizing agents include: ferrocenium, hydrocarbyl-substituted ferrocenium, Ag$^+$, and Pb$^{2+}$.

The quantity of activator compound in the supported catalyst component and the supported catalyst is not critical, but typically ranges from 0.1, preferably from 1 to 2,000 micromoles of activator compound per gram of treated support material. Preferably, the supported catalyst or component contains from 10 to 1,000 micromoles of activator compound per gram of treated support material.

Generally, the ratio of moles of activator compound (b) to gramatoms of transition metal in compound (c) in the supported catalyst is from 0.05:1 to 100:1, preferably from 0.5:1 to 20:1 and most preferably from 1:1 to 5:1 mole activator compound per gramatom of transition metal in the transition metal compound. At too low ratios the supported catalyst will not be very active, whereas at too high ratios the catalyst becomes less economic due to the relatively high cost associated with the use of large quantities of activator compound.

The supported catalyst according to this embodiment can be prepared by combining the support material with the organometal compound and the activator compound. The order of addition is not critical. The organometal compound may be either first combined with the support material or with the activator compound, and subsequently the activator compound or the support material may be added. One preferred embodiment comprises treating the support material first with the organometal compound by combining the organometal compound in a suitable solvent, such as a hydrocarbon solvent, with the support material. The temperature, pressure, and contact time for this treatment are not critical, but generally vary from −20° C. to about 150° C., from subatmospheric to 10 bar, more preferably at atmospheric pressure, for 5 minutes to 48 hours. Usually the slurry is agitated. After this treatment the solids are typically separated from the solvent. Any excess of organometal compound could then be removed by techniques known in the art. This method is especially suitable for obtaining support material with relatively low metal loadings.

According to a preferred embodiment, the support material is first subjected to a thermal treatment at 100° C. to 1000° C., preferably at about 200° C. to about 850° C. Typically, this treatment is carried out for about 10 minutes to about 72 hours, preferably from about 0.5 hours to 24 hours. Then the thermally treated support material is combined with the organometal compound, preferably AlR'$_3$ wherein R' has the meaning defined hereinbefore in a suitable diluent or solvent, preferably one in which the organometal compound is soluble. Typical solvents are hydrocarbon solvents having from 5 to 12 carbon atoms, preferably aromatic solvents such as toluene and xylenes, or aliphatic solvents of 6 to 10 carbon atoms, such as hexane, heptane, octane, nonane, decane, and isomers thereof, cycloaliphatic solvents of 6 to 12 carbon atoms such as cyclohexane, or mixtures of any of these.

The support material is combined with the organometal compound at a temperature of −20° C. to 150° C., preferably at 20° C. to 100° C. The contact time is not critical and can vary from 5 minutes to 72 hours, and is preferably from 0.5 hours to 36 hours. Agitation is preferably applied. The thus treated support material is then preferably contacted with the activator compound.

An alternative treatment of the support material, suitable for obtaining alumoxane loadings attached to the support material, involves one or both of the following steps A and B:
  A. heating a support material containing alumoxane under an inert atmosphere for a period and at a temperature sufficient to fix alumoxane to the support material;
  B. subjecting the support material containing alumoxane to one or more wash steps to remove alumoxane not fixed to the support material;
  thereby selecting the conditions in heating step A and washing step B so as to form a treated support material wherein not more than about 10 percent aluminum present in the treated support material cis extractable in a one hour extraction with toluene of 90° C. using about 10 mL toluene per gram of supported catalyst component. High amounts of alumoxane attached to the support material are obtained using first heating step A., optionally followed by wash step B.

In this process the alumoxane treated support material may be obtained by combining in a diluent an alumoxane with a support material containing from zero to not more than 20 weight percent of water, preferably from zero to not more than 6 weight percent of water, based on the total weight of support material and water. The alumoxane desirably is used in a dissolved form.

Alternatively, the alumoxane pretreated support material may be obtained by combining in a diluent, a support material containing from 0.5 to 50 weight percent water, preferably from 1 to 20 weight percent water, based on the total weight of support material and water, with a compound of the formula R"$_{n*}$AlX"$_{3-n*}$ wherein R" in independently each occurrence is a hydrocarbyl radical, X" is halogen or hydrocarbyloxy, and n* is an integer from 1 to 3. Preferably, n* is 3. R" in independently each occurrence is preferably an alkyl radical, advantageously one containing from 1 to 12 carbon atoms. Preferred alkyl radicals are methyl, ethyl, propyl, isopropyl, n-butyl, isobutyl, tert-butyl, pentyl, iso-pentyl, hexyl, iso-hexyl, heptyl, octyl, and cyclohexyl. Highly preferred compounds of formula R"$_{n*}$AlX"$_{3-n*}$ are trimethylaluminum, triethylaluminum and tri-isobutylaluminum. When the alumoxane is prepared in situ by reacting the compound of the formula R"$_{n*}$AlX"$_{3-n*}$ with water, the mole ratio of R"$_{n*}$AlX"$_{3-n*}$ to water is typically 10:1 to 1:1, preferably from 5:1 to 1:1.

The support material is added to the alumoxane or compound of the formula R"$_{n*}$AlX"$_{3-n*}$, preferably dissolved in a solvent, most preferably a hydrocarbon solvent, or the solution of alumoxane or compound of the formula R"$_{n*}$AlX"$_{3-n*}$ is added to the support material. The support material can be used as such in dry form or slurried in a hydrocarbon diluent. Both aliphatic and aromatic hydrocarbons can be used. Suitable aliphatic hydrocarbons include, for example, pentane, isopentane, hexane, heptane, octane, iso-octane, nonane, isononane, decane, cyclohexane, methyl-cyclohexane and combinations of two or more of such diluents. Suitable examples of aromatic diluents are benzene, toluene, xylene, and other alkyl or halogen-substituted aromatic compounds. Most preferably, the diluent is an aromatic hydrocarbon, especially toluene. Suitable concentrations of solid support in the hydrocarbon medium range from about 0.1 to about 15, preferably from about 0.5 to about 10, more preferably from about 1 to about 7 weight percent. The contact time and temperature are not critical. Preferably the temperature is from 0° C. to 60° C., more preferably from 10° C. to 40° C. The contact time is from 15 minutes to 40 hours, preferably from 1 to 20 hours.

Before subjecting the alumoxane-treated support material to the heating step or washing step, the diluent or solvent is preferably removed to obtain a free flowing powder. This is preferably done by applying a technique which only removes the liquid and leaves the aluminum compounds on the solid, such as by applying heat, reduced pressure, evaporation, or a combination thereof. If desired, the removal of diluent can be combined with the heating step, although care should be taken that the diluent is removed gradually.

The heating step and/or the washing step are conducted in such a way that a very large proportion (more than about 90 percent by weight) of the alumoxane which remains on the support material is fixed. Preferably, a heating step is used, more preferably a heating step is used followed by a washing step. When used in the preferred combination both steps cooperate such that in the heating step the alumoxane is fixed to the support material, whereas in the washing step the alumoxane which is not fixed is removed to a substantial degree. The upper temperature for the heat-treatment is preferably below the temperature at which the support material begins to agglomerate and form lumps which are difficult to redisperse, and below the alumoxane decomposition temperature. When the transition metal compound c) is added before the heat treatment, the heating temperature should be below the decomposition temperature of the transition metal compound. Preferably, the heat-treatment is carried out at a temperature from 90° C. to 250° C. for a period from 15 minutes to 24 hours. More preferably, the heat treatment is carried out at a temperature from 160° C. to 200° C. for a period from 30 minutes to 4 hours. Good results have been obtained while heating for 8 hours at 100° C. as well as while heating for 2 hours at 175° C. By means of preliminary experiments, a person skilled in the art will be able to define the heat-treatment conditions that will provide the desired result. It is also noted, that the longer the heat treatment takes, the higher the amount of alumoxane fixed to the support material will be. The heat-treatment is carried out at reduced pressure or under an inert atmosphere, such as nitrogen gas, or both but preferably at reduced pressure. Depending on the conditions in the heating step, the alumoxane may be fixed to the support material to such a high degree that a wash step may be omitted.

In the wash step, the number of washes and the solvent used are such that sufficient amounts of non-fixed alumoxane are removed. The washing conditions should be such that non-fixed alumoxane is soluble in the wash solvent. The support material containing alumoxane, preferably already subjected to a heat-treatment, is preferably subjected to one to five wash steps using an aromatic hydrocarbon solvent at a temperature from 0° C. to 110° C. More preferably, the temperature is from 20° C. to 100° C. Preferred examples of aromatic solvents include toluene, benzene and xylenes. More preferably, the aromatic hydrocarbon solvent is toluene. At the end of the wash treatment, the solvent is removed by a technique that also removes the alumoxane dissolved in the solvent, such as by filtration or decantation. Preferably, the wash solvent is removed to provide a free flowing powder.

The organometal compound treated support material is then typically reslurried in a suitable diluent and combined with the activator compound. The activator compound is preferably used in a diluent. Suitable diluents include hydrocarbon and halogenated hydrocarbon diluents. Any type of solvent or diluent can be used which does not react with the catalyst components in such a way as to negatively impact the catalytic properties. Preferred diluents are aromatic hydrocarbons, such as toluene, benzene, and xylenes, and aliphatic hydrocarbons such as hexane, heptane, and cyclohexane. Preferred halogenated hydrocarbons include methylene chloride and carbon tetrachloride. The temperature is not critical but generally varies between −20° C. and the decomposition temperature of the activator. Typical contact times vary from a few minutes to several days. Agitation of the reaction mixture is preferred. Advantageously, the activator compound is dissolved, using heat to assist in dissolution where desired. It may be desirable to carry out the contacting between the organometal-treated support material and the activator compound at elevated temperatures. Preferably, such elevated temperatures are from 45° C. to 120° C.

Instead of first treating the support material with the organometal compound, preferably aluminum component, and subsequently adding the activator compound, the organometal compound, preferably aluminum component, and activator compound may be combined in a suitable diluent prior to adding or combining the reaction mixture to or with the support material.

Without wishing to be bound by any theory, it is believed that an organo group of the organometal compound reacts with the active hydrogen moiety contained in the activator anion (b-2) to form a reaction or contact product (hereinafter also referred to as "adduct"). For example, when the organometal compound is trialkylaluminum $AlR_3$ and the active hydrogen-containing moiety is represented by G-OH, the reaction product is believed to comprise G-O—$AlR_2$ whereas further an alkane by-product RH is formed. This adduct G-O—$AlR_2$ when combined with the support material containing hydroxyl groups, Si—OH in case of a silica support material, is believed to form Si—O—Al(R)—O-G together with alkane RH as by-product. This method of preparing the supported catalyst component has been found to run very smoothly and to provide catalysts and catalyst precursors or components having desirable properties. Typical ratios to be used in this reaction are from about 1:1 to about 20:1 moles of organometal compound to mole equivalents of active hydrogen moieties contained in the activator anion (b-2).

The amount of adduct, formed by combining the organometal compound with the activator compound, to be combined with the support material is not critical. Preferably, the amount is not higher than can be fixed to the support material. Typically, this is determined by the amount of support material hydroxyls. The amount of adduct to be employed is preferably not more than the equivalent amount of such hydroxyl groups. Less than the equivalent amount is preferably used, more preferably the ratio between moles of adduct to moles of surface reactive groups such as hydroxyls is between 0.01 and 1, even more preferably between 0.02 and 0.8. Prior to adding the transition metal compound it is preferred, especially when less than an equivalent amount of adduct is added with respect to surface reactive groups, to add an additional amount of organometal compound to the reaction product of support material and the adduct to remove any remaining surface reactive groups which otherwise may react with the transition metal and thus require higher amounts thereof to achieve equal catalytic activity. Prior to combining it with the transition metal compound, the supported catalyst component can be washed, if desired, to remove any excess of adduct or organometal compound.

The supported catalyst component comprising the support material, organometal compound, and the activator may be isolated to obtain a free flowing powder by removing the liquid medium using preferably filtration or evaporation techniques.

Although the transition metal compound may be combined with the activator compound, or the adduct of the organometal compound and the activator compound, prior to combining the activator compound or its adduct with the support material, this results in reduced catalyst efficiencies. Preferably, the transition metal is first combined with the support material treated with the organometal component and before adding the activator compound, or the transition metal is added after the treated support material and activator have been combined, or after the activator adduct and the support material have been combined. Most preferably, the transition metal compound (c) is added to the reaction product of the support material treated with the organometal compound and activator compound, or after the activator adduct and the support material have been combined.

The transition metal compound is preferably used dissolved in a suitable solvent, such as a hydrocarbon solvent, advantageously a $C_{5-10}$ aliphatic or cycloaliphatic hydrocarbon or a $C_{6-10}$ aromatic hydrocarbon. The contact temperature is not critical provided it is below the decomposition temperature of the transition metal and of the activator. Good results are obtained in a temperature range of 0° C. to 100° C. All steps in the present process should be conducted in the absence of oxygen and moisture.

Upon combining the transition metal compound with the supported catalyst component, the supernatant liquid typically is colorless indicating that the transition metal compound, which solution typically is colored, substantially remains with the solid supported catalyst.

According to an alternative preferred embodiment the solid (or supported) catalyst comprises:

a supported catalyst component comprising a support material and an alumoxane wherein not more than about 10 percent aluminum present in the supported catalyst component is extractable in a one hour extraction with toluene of 90° C. using about 10 ml toluene per gram of supported catalyst component;

and a transition metal compound.

This solid catalyst according to this embodiment may be used in the absence of the activator compound (b) comprising (b-1) a cation which is capable of reacting with a transition metal compound to form a catalytically active transition metal complex, and (b-2) a compatible anion having up to 100 nonhydrogen atoms and containing at least one substituent comprising an active hydrogen moiety.

According to this alternative embodiment, the aluminum atom (from the alumoxane component) to transition metal atom mole ratio in the supported catalyst generally is from 1 to 5000, preferably from 25 to 1000 and most preferably from 50 to 500.

The quantity of transition metal compound in the supported catalyst of the present invention is not critical, but typically ranges from 0.1 to 1000 micromoles of transition metal compound per gram of support material. Preferably, the supported catalyst contains from 1 to 250 micromoles of transition metal compound per gram of support material.

The supported catalyst according to this embodiment is obtainable by heating and/or washing a support material containing alumoxane under an inert atmosphere for a period and at a temperature sufficient to fix alumoxane to the support material, as discussed above.

It may be advantageous to use in the present process the solid catalyst in association with impurity scavengers which serve to protect the solid catalyst from catalyst poisons such as water, oxygen, and polar compounds. Preferred compounds for this purpose include an organoaluminum compound represented by the following formula:

wherein R is a $C_1$-$C_{20}$ hydrocarbyl group; X is a halogen atom or a $C_1$-$C_{20}$ hydrocarbyloxy group; and n is a positive integer selected from 1 to 3, or an organoaluminumoxy compound represented by the following formula:

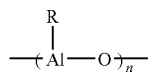

wherein R is a $C_1$-$C_{20}$ hydrocarbyl group; and n is a positive integer selected from 5 to 50.

By the treatment with the organoaluminum compound or the organoaluminumoxy compound, the resistance of the solid catalyst system to impurities, such as water, oxygen and the like which are present in the solid catalyst system, can be improved, and the solid catalyst system can be stored for a prolonged period of time.

In the above treatment, the organoaluminum compound or the organoaluminumoxy compound is used preferably in an amount of 0.1 to 100 mol in terms of aluminum, more preferably in an amount of 1 to 30 mol, per mol of a transition metal compound contained in the solid catalyst system. It is noted that the organoaluminiumoxy compound should preferably not be used in amount that may cause desorption of the transition metal compound from the solid catalyst.

The solid catalyst system to be used in the method of the present invention can be stored in the form of a slurry thereof in an inert hydrocarbon solvent, or dried and stored in a solid form thereof.

When a copolymerization reaction for producing the ethylene copolymer of the present invention is conducted using the solid catalyst system, it is important that the copolymerization reaction be performed under conditions such that the reaction rate is limited by independent diffusion of each of the polymerization participants (such as hydrogen, ethylene and at least one comonomer) into the ethylene copolymer being formed. For this purpose, the copolymerization reaction must be conducted under conditions such that the ethylene copolymer being formed around the solid catalyst system is not melted or dissolved in the reaction system.

For realizing the above-mentioned polymerization reaction conditions, the copolymerization reaction is conducted by slurry polymerization.

By conducting slurry polymerization under the above-mentioned reaction conditions, as long as the reaction conditions are appropriately controlled, the ethylene copolymer being formed around the solid catalyst system is not melted or dissolved during the polymerization reaction, but maintains a powdery form (which powdery form is achieved by the use of the above-mentioned specific catalyst system) during the reaction, so that one of the above-mentioned requirements for enabling the polymerization reaction to proceed at a diffusion-limited rate, such that the produced copolymer must not be melted in the reaction mixture but maintains the solid state, can be satisfied.

When a copolymerization reaction is conducted by slurry polymerization, a polymerization pressure is generally from 1 to 100 atm, preferably from 3 to 30 atm, and a polymerization temperature is generally from 20 to 115° C., preferably from 50 to 105° C. However, the upper limit of the polymerization temperature is a temperature which is highest among temperatures at which the ethylene copolymer produced can maintain substantially a powdery state. Such a highest temperature varies depending on the density of the ethylene copolymer produced and the type of a solvent used.

As a solvent to be used for slurry polymerization, the inert solvents, which are mentioned above in connection with the preparation of the solid catalyst system, can be suitably used. Especially, isobutane, isopentane, heptane, hexane and octane are preferred.

As mentioned above, in the present invention, it is important that the ethylene copolymer produced must maintain a powdery state during the polymerization reaction. Therefore, the upper limit of the polymerization temperature is extremely important.

In the method of the present invention, as mentioned above, ethylene is copolymerized with at least one comonomer. Typical reactors for the polymerization can include slurry loop reactors or autoclaves.

As mentioned above, at least one comonomer to be used in the method of the present invention is selected from the group comprising a compound represented by the formula $H_2C\!\!=\!\!CHR$ wherein R is a $C_1$-$C_{20}$ linear, branched or cyclic alkyl group or a $C_6$-$C_{20}$ aryl group, and a $C_4$-$C_{20}$ linear, branched or cyclic diene. Illustrative examples of the compounds represented by the formula $H_2C\!\!=\!\!CHR$ include propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, vinylcyclohexene and styrene. Illustrative examples of $C_4$-$C_{20}$ linear, branched and cyclic dienes include 1,3-butadiene, 1,4-pentadiene, 1,5-hexadiene, 1,4-hexadiene and cyclohexadiene. Of these, propylene, 1-butene, 1-pentene, 1-hexene, 4-methyl-1-pentene, 1-octene, 1-decene, 1-dodecene, 1-tetradecene, 1-hexadecene, 1-octadecene and 1-eicosene are especially preferred.

In producing the ethylene copolymer, the molecular weight of the ethylene copolymer produced can be controlled by changing the content of hydrogen in the reaction system or by changing the polymerization temperature, as described in DE 3127133.2.

In the present invention, the solid catalyst system may contain, in addition to the above-mentioned components, various additives which are known to be useful for the ethylene copolymerization. Additives such as antioxidants (e.g., hindered phenolics (e.g., Irganox™ 1010), phosphites (e.g., Irgafos™ 168)), cling additives (e.g., PIB), antiblock additives, pigments, fillers, and the like can also be included in the formulations, to the extent that they do not interfere with the enhanced formulation properties discovered by Applicants. Both Irganox™ and Irgafos™ are made by and trademarks of Ciba Geigy Corporation. Irgafos™ 168 is a phosphite stabilizer and Irganox™ 1010 is a hindered polyphenol stabilizer (e.g., tetrakis [methylene 3-(3,5-di t-butyl-4-hydroxyphenyl-propionate)]-methane.

Blend Compositions.

The copolymer of present invention can be used in blend compositions comprising said novel ethylene copolymer and:
- a) a second ethylene copolymer of the present invention of different molecular weight or density; or
- b) a homogeneous narrow composition distribution ethylene/☐-olefin interpolymer;
- c) a heterogeneous broad distribution ethylene/☐-olefin interpolymer; or
- d) a homopolymer, or
- e) a combination of any two or more of a), b) c) or d).

a) Blend Compositions Comprising a Second Ethylene Copolymer of the Present Invention of Different Molecular Weight and Density.

Blends compositions comprising the ethylene copolymer with a second ethylene copolymer of the present invention of different molecular weight or density, are highly advantageous. As long as the method of the present invention is essentially applied to the production of an ethylene copolymer, any of a method in which one or more different ethylene copolymers of this invention and each having excellent ESCR properties and different comonomer contents are separately produced using this method and blended by means of a kneader (hereinafter, frequently referred to as "blending-and-kneading method") and a method in which an ethylene copolymer comprising a mixture of two or more different ethylene copolymer components having different comonomer contents is produced by multi-stage polymerization or using a plurality of different types of catalysts to be used in the present invention, can be very advantageously utilized. Further, an ethylene copolymer comprised of a mixture of two or more different ethylene copolymer components having different comonomer contents can be produced by using a plurality of different types of catalysts to be used in the present invention, not only can the impact resistance and ESCR properties be further improved, but also a markedly improved balance of various properties, such as impact resistance, rigidity, melt-flow characteristics and the like, can be achieved.

b) Blend Compositions Comprising Homogeneous Narrow Composition Distribution Ethylene/α-Olefin Interpolymers.

Blends compositions comprising the ethylene copolymer with homogeneous narrow composition interpolymers, most preferably the substantially linear ethylene/α-olefin interpolymers are also highly advantageous. The homogeneous interpolymer components of the blend compositions are herein defined as defined in U.S. Pat. No. 3,645,992 (Elston), the disclosure of which is incorporated herein by reference. Accordingly, homogeneous interpolymers are those in which the comonomer is randomly distributed within a given interpolymer molecule and wherein substantially all of the interpolymer molecules have the same ethylene/comonomer ratio within that interpolymer. Such interpolymers are distinct from the typical Ziegler catalyzed interpolymers which are known as heterogeneous interpolymers and are those in which the interpolymer molecules do not have the same ethylene/comonomer ratio. The homogeneous polymers are also distinct from LDPE produced by high pressure free radical catalyzed ethylene polymerization which results in highly branched polyethylene which is known to those skilled in the art to have numerous long chain branches.

The term "narrow composition distribution" used herein describes the comonomer distribution for homogeneous interpolymers and means that the homogeneous interpolymers have only a single melting peak as measured by Differential Scanning Calorimetry (DSC) and essentially lack a measurable "linear" polymer fraction.

The narrow composition distribution homogeneous interpolymers can also be characterized by their SCBDI (Short Chain Branch Distribution Index) or CDBI (Composition Distribution Branch Index) which is defined as the weight percent of the polymer molecules having a comonomer content within 50 percent of the median total molar comonomer content. The CDBI of a polymer is readily calculated from data obtained from techniques known in the art, such as, for example, temperature rising elution fractionation (abbreviated herein as "TREF") as described, for example, in Wild et al, *Journal of Polymer Science, Poly. Phys. Ed.*, Vol. 20, p. 441 (1982), in U.S. Pat. No. 4,798,081 (Hazlitt et al.), or as is described in U.S. Pat. No. 5,008,204 (Stehling), the disclosure of which is incorporated herein by reference. The technique for calculating CDBI is described in U.S. Pat. No. 5,322,728 (Davey et al.) and in U.S. Pat. No. 5,246,783 (Spenadel et al.) or in U.S. Pat. No. 5,089,321 (Chum et al.) the disclosures of all of which are incorporated herein by reference. The SCBDI or CDBI for the homogeneous narrow composition ethylene/α-olefin interpolymers used in the present invention is preferably greater than about 50 percent, especially greater than about 70 percent, most preferably greater than about 90%.

The narrow composition distribution homogeneous interpolymer blend components of this invention essentially lack a measurable "high density" (or homopolymer) fraction as measured by the TREF technique. The homogeneous interpolymers and polymers have a degree of branching less than or equal to 2 methyls/1000 carbons in about 15 percent (by weight) or less, preferably less than about 10 percent (by weight), and especially less than about 5 percent (by weight).

Preferred components of the blends of the current invention are the substantially linear ethylene/α-olefin interpolymers. The substantially linear ethylene/α-olefin interpolymers are herein defined as in U.S. Pat. Nos. 5,272,236 and 5,278,272 by Lai et al (U.S. Pat. Nos. 5,272,236 and 5,278, 272), the teachings of which contained therein, are herein incorporated in their entirety by reference.

c) Blend Compositions Comprising the Heterogeneous Broad Composition Distribution Ethylene/α-Olefin Interpolymers.

Blends compositions comprising the ethylene copolymer with the heterogeneous broad composition distribution ethylene interpolymers are also highly adavntageous. Included in the definition of heterogeneous interpolymers as used herein are those produced using Ziegler catalysts and also those produced by the chromium-based silica-supported systems, commonly known as the Phillips-type catalysts.

The term heterogeneous describes interpolymers in which the interpolymer molecules do not have the same ethylene/comonomer ratio. The term "broad composition distribution" used herein describes the comonomer distribution for heterogeneous interpolymers and means that the heterogeneous interpolymers have a "linear" fraction and that the heterogeneous interpolymers have multiple melting peaks (i.e., exhibit at least two distinct melting peaks) by DSC. The heterogeneous interpolymers and polymers have a degree of branching less than or equal to 2 methyls/1000 carbons in about 10 percent (by weight) or more, preferably more than about 15 percent (by weight), and especially more than about 20 percent (by weight). The heterogeneous interpolymers also have a degree of branching equal to or greater than 25 methyls/1000 carbons in about 25 percent or less (by weight), preferably less than about 15 percent (by weight), and especially less than about 10 percent (by weight).

c) Blend Compositions Comprising a Homopolymer.

Blend compositions comprising the copolymer of the present invention with a homopolymer are also highly advantageous. Such homopolymers can include those produced by the Ziegler or single site metallocene catalysts and also those produced by the chromium-based silica-supported systems, commonly known as the Phillips-type catalysts.

INDUSTRIAL APPLICABILITY

The ethylene copolymer of the present invention has a specific comonomer content distribution characteristic, wherein, in one aspect, the lower the molecular weight of a copolymer fraction in a molecular weight distribution of an ethylene copolymer, the lower the comonomer content of the copolymer fraction; and, in the other aspect, the higher the molecular weight of a copolymer fraction, the higher the comonomer content of the copolymer fraction. By virtue of this comonomer content distribution characteristic, the ethylene copolymer of the present invention has excellent properties, such as high impact strength and excellent environmental stress cracking resistance (ESCR). Further, the ethylene copolymer of the present invention does not exhibit a broad tailing on both the low molecular weight side and the high molecular weight side, so that the ethylene copolymer contains substantially no impurities such as a wax, a gel and the like. Further, as long as the method of the present invention is essentially applied to the production of an ethylene copolymer, any of a method in which two or more different ethylene copolymers having different comonomer contents are separately produced and blended by means of a kneader, and a method in which an ethylene copolymer comprising a mixture of two or more different ethylene copolymer components having different comonomer contents is produced by multi-stage polymerization or using a plurality of different types of catalysts to be used in the present invention, can be very advantageously utilized in a preferred mode of the method of the present invention. The mixture of the ethylene copolymers produced by the above-mentioned preferred method of the present invention can have a comonomer content distribution in which the comonomer content continuously varies in accordance with an increase in molecular weight of the copolymer, contrary to that of the mixture of conventional ethylene copolymers. Thus, according to the above-mentioned slurry method of the present invention, excellent characteristic can be obtained with respect to the comonomer content distribution of the mixture of the ethylene copolymers, which has not been achieved by the prior art techniques.

Due to the above-mentioned excellent properties and characteristics, the ethylene copolymer of the present invention can be advantageously used for the production of film, fibers, foams or sheets including blown film, cast films, laminate films, blow-molded articles, injection molded articles, coating materials for cables, and the like. These can be further fabricated into pipes, tubing, cable or wire jackets, pipe coatings, geomembranes, thermoformed articles, stackable plastic pallets, blow molded bottles or containers, or environmental pond liners

EXAMPLES

The present invention will now be further illustrated in more detail with reference to the following Examples and Comparative Examples, which should not be construed as limiting the scope of the present invention.

Example 1

20 g of silica SP-9-10046 (manufactured and sold by Grace GmbH, Germany), which had been treated at 250° C. for 2 hours under vacuum, was slurried in 250 ml of toluene. To the resultant slurry was added a solution of 20 ml (0.11 mol) of triethylaluminum in 100 ml of toluene. The resultant mixture was stirred for 2 hours, filtered, washed with two 100 ml portions of fresh toluene and dried under vacuum. The resultant 22 g of dried mixture was slurried in 300 ml of toluene and heated to 70° C. to thereby obtain a slurry. To this slurry was added a solution of 1.25 g (1.77 mmol) of triethylammonium tris(pentafluorophenyl)(4-hydroxyphenyl)borate in 200 ml of toluene which had been heated to and maintained at 70° C. for 30 minutes. Upon addition the heating was removed and the resultant mixture was stirred for 3 hours. After that, a 12.3 ml aliquot of a dark violet colored 0.0714M solution of titanium (N-1,1-dimethylethyl)dimethyl[1-(1,2,3,4,5,-eta)-2,3,4,5-tetramethyl-2,4-cyclopentadien-1-yl]silanaminato[(2-)N]-$\eta^4$-1,3-pentadiene) in ISOPAR™ E(manufactured and sold by Exxon Chemical Co., USA) was added to the mixture and the resultant mixture was stirred for 2 hours to thereby obtain a green colored solid catalyst system.

Isopentane, ethylene, 1-butene, hydrogen and the solid catalyst system were continuously fed to a 10-liter jacketed, continuously stirred tank reactor. The. flow rates of isopentane, ethylene, 1-butene and hydrogen were, respectively, 2,500 g/hr, 700 g/hr, 20 g/hr and 0.3 liter/hr. The slurry product formed was continuously withdrawn from the reactor. The total pressure of the reactor was 15 atm and the internal temperature of the reactor was maintained at 70° C. The slurry withdrawn was fed to a flash tank to remove the diluent and the dry, free flowing ethylene copolymer powder was obtained.

The ethylene copolymer thus obtained had the following properties: a density by ASTM D-792 of 0.929 g/cm$^3$; a melt index of 0.50 g/10 minutes as measured by ASTM D-1238 at 190° C. under a load of 2.16 kg; an Mw of 152,000 and an $M_w/M_n$ of 4.5, both as measured by GPC; an Mt (a point in molecular weight on a molecular weight distribution profile as measured by GPC at which the profile showed a peak having a maximum intensity) of 69,000; an approximate straight line obtained from the comonomer content distribution profile) had a gradient of 0.0013 within the range of from 22,000 to 220,000 in terms of a molecular weight Mc which satisfies the formula log (69,000)–log(Mc)≦0.5; a temperature (at which a maximum amount of extraction was exhibited) of 86° C. as measured by CFC; in CFC an approximate straight line having a gradient of −0.053 was obtained from the relationship between an arbitrary temperature falling within the range of between 86° C. and 96° C. and a point on a molecular weight distribution profile of a copolymer fraction extracted at the arbitrary temperature, which point had a peak having a maximum intensity; and the total amount of copolymer fractions extracted at temperatures of 76° C. or less in CFC was 3.1 wt %.

Examples 2 and 3

25 g of silica SP-9-10046 (manufactured and sold by Grace GmbH, Germany) having a water content of about 3.5% by weight was added to 508 g of 10% methylalumoxane solution in toluene (manufactured and sold by Witco GmbH, Germany) while continuously stirring. The mixture was stirred for a further two hours and then the solvent was removed under reduced pressure at 20° C. to yield a free-flowing powder. The resulted free-flowing powder was then heated at 175° C. for two hours under vacuum. The resulting powder was re-slurried in 700 ml of toluene and the mixture was washed with two portions of fresh toluene at 100° C. The support was then dried under vacuum at 120° C. for 1 hour. 63.9 g of support was obtained having an aluminum content of 26.4% by weight.

To 60 gram of the support was added a 33.6 ml aliquot of a dark violet 0.0714 M solution of titanium (N-1,1-dimethylethyl)dimethyl[1-(1,2,3,4,5-eta)-2,3,4,5-tetramethyl-2,4-cyclopentadien-1-yl]silanaminato[(2-)N]-(eta$^4$-1,3-pentadiene) in ISOPAR™ E (manufactured and sold by EXXON Chemical Co., USA) and the mixture stirred for several hours to yield a green colored supported catalyst.

Substantially the same polymerization procedures as in Example 1 were repeated, except that the flow rates of isopentane, ethylene, 1-butene and hydrogen were changed as indicated in Table 1. The results of the reactions are shown in Table 1.

Examples 4 to 6

Substantially the same procedures were used as in Examples 2 and 3 to produce the supported catalyst, except that a different MAO treated silica was used wherein the MAO was also immobilized on the silica, but using a different method.

Substantially the same polymerization procedures as in Example 1 were used, except that the polymerization temperatures and the flow rates of isopentane, 1-butene and hydrogen were changed as indicated in Table 1. The gradient and CFC 1 and CFC 2 data for Examples 4-6 are extrapolates, based on density, from the results of Example 1-3.

The results of the reactions are shown in Table 1.

Example 7

6.2 g (8.8 mmol) of triethylammonium tris(pentafluorophenyl)(4-hydroxyphenyl)borate was dissolved in 4 liter of toluene which had been heated to and maintained at 90° C. for 30 minutes. To this solvent was added a 40 ml aliquot of a 1M solution of triehexylaluminum in toluene. The resultant mixture was stirred for 1 min at 90° C. On the other hand 100 g of silica P-10 (manufactured and sold by Fuji silysia, Japan), which had been treated at 500° C. for 3 hours in flowing nitrogen, was slurried in 1.7 liter of toluene. This silica slurry was heated to 90° C. To this silica slurry was added said mixture of triethylammonium tris(pentafluorophenyl)(4-hydroxyphenyl)borate and triethylaluminum keeping 90° C., and stirred for 3 hours at 90° C. To the resultant was added a 206 ml aliquot of a 1 M solution of trihexylaluminum in toluene. The resultant mixture in about 5.9 liter of toluene was stirred at 90° C. for 1 hours. Then the supernatant of the resultant mixture was removed by decantation method using 90° C. toluene to remove excess trihexylaluminum. The decantation was repeated 5 times. After that, a 20 ml aliquot of a dark violet colored 0.218M solution of titanium (N-1,1-dimethylethyl)dimethyl[1-(1,2,3,4,5,-eta)-2,3,4,5-tetramethyl-2,4-cyclopentadien-1-yl]silanaminato[(2-)N]-($\eta^4$-1,3-pentadiene) in ISOPAR™ E (manufactured and sold by Exxon Chemical Co., USA) was added to the mixture and the resultant mixture was stirred for 3 hours to thereby obtain a green colored solid catalyst system.

Hexane, ethylene, 1-butene, hydrogen and the solid catalyst system were continuously fed to a continuously stirred tank reactor. The flow rates of hexane, ethylene, and hydrogen were, respectively, 46.2 kg/hr, 0.15 kg/hr, 0.15 kg/hr. The flow rates of 1-butene were 0.11 kg/hr (Example 7) and 0.05 kg/hr (Example 8). The slurry product formed was continuously withdrawn from the reactor. The total pressure of the reactor was 10 atm and the internal temperature of the reactor was maintained at 80° C. The slurry withdrawn was fed to a flash tank to remove the diluent and the dry, free flowing ethylene copolymer powder was obtained. The properties of the ethylene copolymers thus obtained are shown in Table 2.

Example 8

200 g of silica P-10 (manufactured and sold by Fuji silysia, Japan), which had been treated at 500° C. for 3 hours in flowing nitrogen, was slurried in 5 liter of hexane. To the resultant slurry was added a 400 ml aliquot of a 1 M solution of triethylaluminum in hexane. The resultant mixture was stirred for 0.5 hour at room temperature. To this slurry was added a solution of 20.1 g (17.6 mmol) of bis(hydrogenated tallowalkyl)methylammonium tris(pentafluorophenyl)(4-hydroxyphenyl)borate in 296 ml of toluene. The resultant mixture was stirred for 0.5 hour at room temperature. After that, a 60 ml aliquot of a dark violet colored 0.218M solution of titanium (N-1,1-dimethylethyl)dimethyl[1-(1,2,3,4,5,-eta)-2,3,4,5-tetramethyl-2,4-cyclopentadien-1-yl]silanaminato[(2-)N]-($\eta^4$-1,3-pentadiene) in ISOPAR™ E (manufactured and sold by Exxon Chemical Co., USA) was added to the mixture and the resultant mixture was stirred for 3 hours at room temperature to thereby obtain a green colored solid catalyst system.

Substantially the same polymerization procedures as in Example 7 were repeated, except that the flow of 1-butene was changed as indicated in Table 1. The results of the reactions are shown in Table 2.

Comparative Example 1

A 1,000 ml flask was charged with 508 g of a 10% solution of methylaluminoxane in toluene (manufactured and sold by Witco GmbH, Germany) and then 25 g of silica SD 3216.30 silica (manufactured and sold by Grace GmbH, Germany) having a water content of about 3.5% by weight was added to the flask while continuously stirring. The resultant mixture was stirred for further 2 hours and then the solvent was removed under reduced pressure at 20° C. to thereby obtain a free flowing powder. The obtained powder was then heated at 175° C. for 2 hours under vacuum. The powder was re-slurried in 700 ml of toluene. The resultant mixture was heated and refluxed for 1 hour. The mixture was filtered, washed with two portions of fresh toluene at 100° C. and dried under vacuum at 120° C. for 1 hour. As a result, 63.9 g of dried mixture having an aluminum content of 23.8% by weight was obtained.

A solid catalyst system was prepared by slurrying 0.5 g of the above-obtained dried mixture in 20 ml of ISOPAR™ E (manufactured and sold by Exxon Chemical Co., USA), stirring for a few minutes to disperse the dried mixture, and adding a 0.142 ml aliquot of a dark orange-brown colored solution of [(tert-butylamido)(dimethyl)(tetramethyl-$\eta^5$-cyclopentadienyl)silane dimethyltitanium. The resultant mixture was stirred for a few minutes to thereby obtain a yellow-orange colored solid catalyst system.

A stirred 3-liter reactor was charged with 1,191 ml of ISOPAR™ E (manufactured and sold by Exxon Chemical Co., USA), 309 ml of 1-octene and 0.3 liter of hydrogen. The reactor contents were heated to 80° C. and ethylene was added to the reactor in an amount sufficient to bring the total pressure of the reactor to about 31 atm. The solid catalyst system containing 1.5 µmol of titanium was added to the reactor to thereby initiate a polymerization reaction. Ethylene was supplied to the reactor continuously on demand. After 21 minutes the ethylene line was blocked and the reactor contents were dumped into a sample container. The resultant copolymer was dried overnight. As a result, 41 g of an ethylene copolymer was obtained.

The ethylene copolymer thus obtained had the following properties: a density of 0.883 g/cm3; an MFR of 0.35 g/10 minutes as measured at 190° C. under a load of 2.16 kg; an Mw of 130,000 and an $M_w/M_n$ of 3.5, both as measured by GPC; an Mt (a point in molecular weight on a molecular weight distribution profile as measured by GPC at which the profile showed a peak having a maximum intensity) of 96,000; an approximate straight line obtained from the comonomer content distribution profile) had a gradient of 0.0030 within the range of from 30,000 to 304,000 in terms of a molecular weight Mc which satisfies the formula log (96,000)–log(Mc)≦0.5; a temperature (at which a maximum amount of extraction was exhibited) of 37° C. as measured by CFC; in CFC an approximate straight line having a gradient of –0.010 was obtained from the relationship between an arbitrary temperature falling within the range of between 37° C. and 47° C. and a point on a molecular weight distribution profile of a copolymer fraction extracted at the arbitrary temperature, which point had a peak having a maximum intensity; and the total amount of copolymer fractions extracted at temperatures of 27 ° C. or less in CFC was 18.5 wt %.

Comparative Example 2

A 200-ml glass flask, which had been fully purged with nitrogen gas, was charged with 4.0 g of silica (manufactured and sold by Fuji Silysia Chemical Ltd., Japan) and 40 ml of toluene. The resultant mixture was stirred to obtain a suspension. The obtained suspension was cooled to –10° C. To the cooled suspension was dropwise added 30 ml of a solution of methylaluminoxane (manufactured and sold by Albemarle Corporation, USA) in toluene (Al concentration: 1 mol/liter) over 1 hour in a nitrogen atmosphere, while maintaining the temperature of the suspension at –10° C. The resultant mixture was maintained at 0° C. for 1 hour and then at room temperature for 1 hour, in the nitrogen atmosphere. Thereafter, the temperature of the mixture was further elevated to 110° C., so that the mixture was refluxed for 3 hours, in the nitrogen atmosphere. During a series of the above operations, generation of methane gas from the mixture was observed. Then, the mixture was cooled to 20° C., so that a suspension of a silica having methylaluminoxane carried thereon was obtained.

A 1.6-liter stainless autoclave, which had been fully purged with nitrogen gas, was charged with 0.8 liter of hexane and then 0.2 mmol of triisobutylaluminum was added to the hexane in the autoclave. To the resultant mixture was added the above-obtained silica suspension in an amount of 0.3 mmol in terms of aluminum of methylaluminoxane carried on the silica. Ethylene was added to the autoclave in an amount sufficient to bring the total pressure of the autoclave to 7kg/cm²-G. The internal temperature of the autoclave was adjusted to 65° C.

A solution of bis(n-butylcyclopentadienyl)zirconium dichloride (which is known as a metallocene) in toluene was added to the autoclave in an amount of 1.0 µmol in terms of zirconium, and the internal temperature of the autoclave was elevated to 70° C., to thereby initiate a polymerization reaction of the ethylene. The ethylene was supplied to the autoclave continuously on demand.

While maintaining the total pressure of the autoclave at 7 kg/cm²-G and maintaining the internal temperature of the autoclave at 70° C., the polymerization reaction was carried out, so that the total consumption of ethylene became 1.5 kg/cm²-G.

After completion of the polymerization reaction, the contents in the autoclave were dumped into a stainless container containing methanol. The resultant mixture was filtered to thereby obtain a polymer. The obtained polymer was dried at 50° C. overnight. As a result, an ethylene copolymer was obtained.

The autoclave was opened and the inside thereof was examined. No polymer adhering to the inner wall of the autoclave was observed.

The ethylene copolymer thus obtained had the following properties: a density of 0.926 g/cm³; an MFR of 2.1 g/10 minutes as measured at 190° C. under a load of 2.16 kg; an Mw of 88,000 and an $M_w/M_n$ of 2.6, both as measured by GPC; an Mt (a point in molecular weight on a molecular weight distribution profile as measured by GPC at which the profile showed a peak having a maximum intensity) of 63,000; an approximate straight line obtained from the comonomer content distribution profile) had a gradient of –0.00005 within the range of from 20,000 to 199,000 in terms of a molecular weight Mc which satisfies the formula log (63,000)–log(Mc)≦0.5; a temperature (at which a maximum amount of extraction was exhibited) of 85° C. as measured by CFC; in CFC an approximate straight line having a gradient of –0.006 was obtained from the relationship between an arbitrary temperature falling within the range of between 85° C. and 95° C. and a point on a molecular weight distribution profile of a copolymer fraction extracted at the arbitrary temperature, which point had a peak having a maximum intensity; and the total amount of copolymer fractions extracted at temperatures of 75° C. or less in CFC was 10.8 wt %.

Comparative Example 3

A stirred 3-liter reactor was charged with 1,388 ml of ISOPAR™ E (manufactured and sold by Exxon Chemical Co., USA), 128 ml of 1-octene and 0.3 liter of hydrogen. The reactor contents were heated to 130° C. and ethylene was added to the reactor in an amount sufficient to bring the total pressure of the reactor to about 31 atm.

A solid catalyst system containing 0.625 µmol of titanium, which was prepared in substantially the same manner as in Example 1, was added to the reactor to thereby initiate a polymerization reaction. Ethylene was supplied to the reactor continuously on demand. After 10 minutes the ethylene line was blocked and the reactor contents were dumped into a sample container. The resultant polymer was dried overnight, to thereby obtain 30 g of an ethylene copolymer.

The ethylene copolymer thus obtained had the following properties: a density of 0.912 g/cm³; an MFR of 4.5 g/10 minutes as measured at 190° C. under a load of 2.16 kg; an Mw of 130,000 and an $M_w/M_n$ of 2.5, both as measured by GPC; an Mt (a point in molecular weight on a molecular weight distribution profile as measured by GPC at which the profile showed a peak having a maximum intensity) of 50,000; an approximate straight line obtained from the comonomer content distribution profile) had a gradient of 0.00003 within the range of from 16,000 to 158,000 in terms of a molecular weight Mc which satisfies the formula log (50,000)–log(Mc)≦0.5; a temperature (at which a maximum amount of extraction was exhibited) of 74° C. as measured by CFC; in CFC an approximate straight line having a gradient of −0.033 was obtained from the relationship between an arbitrary temperature falling within the range of between 74° C. and 84° C. and a point on a molecular weight distribution profile of a copolymer fraction extracted at the arbitrary temperature, which point had a peak having a maximum intensity; and the total amount of copolymer fractions extracted at temperatures of 64° C. or less in CFC was 13.4 wt %.

Comparative Example 4

A commercially available ethylene copolymer, EXACT™ 3029 (manufactured and sold by Exxon Chemical Co., USA), was analyzed. The results of the analysis are shown in Table 2.

Comparative Example 5

A commercially available ethylene copolymer, SP 2040 (manufactured and sold by Mitsui Petrochemical Industries, Ltd., Japan), was analyzed. The results of the analysis are shown in Table 2.

Comparative Example 6

A commercially available ethylene copolymer, PL 1880 (manufactured and sold by The Dow Chemical Co., USA), was analyzed. The results of the analysis are shown in Table 2.

In Table 2, the properties of the ethylene copolymer of the present invention, which was obtained in Example 1, are indicated together with those of the ethylene copolymers which were individually obtained in Comparative Examples 1 to 3 and those of the commercially available ethylene copolymers in Comparative Examples 4 to 6. It is apparent that any of the ethylene copolymers in Comparative Examples 1 to 6 do not have the properties which match those of the ethylene copolymer of the present invention.

Comparative Example 7

A magnesium-chloride supported Ziegler-Natta catalysts having about 2 wt % of Ti on the surface of the support was used for the polymerization.

Hexane, ethylene, 1-butene, hydrogen and the solid catalyst system were continuously fed to a continuously stirred tank reactor to produce the copolymer powder, the properties of which are shown in Table 2.

Examples 9-12

Substantially the same polymerization procedures as in Example 1 were used, except that the transition metal complex used to prepare components 1 and 2 was [(tert-butylamido)(dimethyl)(tetramethyl-$\eta^5$-cyclopentadienyl)-silane dimethyltitanium and the flow rates of isopentane, 1-butene and hydrogen were changed to produce the polymer properties for Components I and II summarized in Table 3. The blends were prepared in a Winkworth 2Z-blade mixer. This internal mixer is equipped with two mixing blades running at different rpm: the front screw rotates at 52 rpm, the rear screw at 30 rpm. The working capacity is 1.2 liters.

The powders were first dry blended with 2000 ppm Irganox® B225 available from Ciba Geigy. Charges of 350 g of the mixture of the desired composition were then loaded and mixed for 10 minutes at 190° C. After mixing the polymer was removed and was milled in a Heinrich Dreher S20 grinder. The ground polymer was then ready for compression molding. The results of the testing of the various blend compositions are shown in Table 4.

Example 13-16

Substantially the same polymerization procedures as in Examples 7 and 8 were repeated to produce the ethylene copolymers used as Component II, except that the flow ratio of hexane, ethylene, 1-butene, hydrogen were adjusted along with the polymerization temperature. The ethylene copolymers produced in Examples 7 and 8 were used as Component I. The polymer properties for Component I and Component II and the blend formulation are summarized in Table 5. The blends were prepared with using the twin-screw extruder (PCM-45, manufactured by IKEGAI, Co., Ltd., Japan). The screw rotates at 100-200 rpm. The screw barrel temperature was 220° C.

The powders were first dry blended with 2000 ppm Irganox® 1076 available from Ciba Geigy, 600 ppm Calcium Stearate, and 1000 ppm P-EPQ® available from Sando. The results of the testing of the various blend compositions are shown in Table 6.

Comparative Example 8-10

Substantially the same polymerization procedures as in Comparative Examples 7 was used to produce the ethylene homopolymers used for Component II. Also, the ethylene copolymer produced in Comparative Examples 7 was used as Component I. The polymer properties for Component I and Component II and the blend formulation are summarized in Table 5. The blends were prepared using the same procedure as in Examples 13-16. The results of the testing of the various blend compositions are shown in Table 6.

Examples 9-16 show the excellent balance of properties such as impact strength at low temperature (as measured by $G_c$ at 0 and −20° C. and by Charpy Impact Strength −20° C.), processability (as measured by V at 100 l/s and by $_{121.6}$), and ESCR (as measured by PENT and by Bending ESCR TEST) for the various blend compositions and that such balance is best achieved by having the comonomer preferentially in the high molecular weight component. Further, it is clear that the Example 13-16 exhibit superior properties compared to those of Comparative Examples 8-10.

TABLE 1

|  | Units | Example 1 | Example 2 | Example 3 | Example 4 | Example 5 | Example 6 | Example 7 | Example 8 |
|---|---|---|---|---|---|---|---|---|---|
| Polymerization Temperature | (° C.) | 70 | 55 | 70 | 30 | 60 | 40 | 80 | 80 |
| Catalyst Activator |  | Borate | MAO | MAO | MAO | MAO | MAO | Borate | Borate |

TABLE 1-continued

|  | Units | Example 1 | Example 2 | Example 3 | Example 4 | Example 5 | Example 6 | Example 7 | Example 8 |
|---|---|---|---|---|---|---|---|---|---|
| Isopentane Flow | (g/hr) | 2500 | 2500 | 2500 | 2500 | 1800 | 3600 |  |  |
| Hexane Flow | (kg/hr) |  |  |  |  |  |  | 46.2 | 46.2 |
| Ethylene Flow | (g/hr) | 700 | 850 | 650 | 850 | 600 | 600 | 5.0 | 5.0 |
| Comonomer Flow | (g/hr) | 20 | 110 | 30 | 200 | 30 | 176 | 0.11 | 0.05 |
| Hydrogen Flow | (g/hr) | 0.3 | 0.3 | 0.65 | 1 | 0.3 | 0.8 | 0.15 | 0.15 |
| Density | (g/cm$^3$) | 0.929 | 0.910 | 0.935 | 0.887 | 0.934 | 0.890 | 0.9295 | 0.9378 |
| MFR | (g/10 min) | 0.5 | 0.02 | 0.36 | 0.07 | 0.07 | 0.23 | 0.012 | 0.013 |
| $M_w/M_n$ |  | 4.5 | 4.2 | 4.1 | 4.8 | 3.5 | 3.8 | 5.50 | 5.81 |
| Gradient*1 |  | 0.0013 | 0.0044 | 0.0011 | 0.0098 | 0.0011 | 0.0086 | 0.0010 | 0.0007 |
| CFC 1*2 |  | −0.053 | −0.026 | −0.061 | −0.015 | −0.061 | −0.017 | −0.008 | −0.205 |
| CFC 2*2 | (wt %) | 3.1 | 1.7 | 3.8 | 1.1 | 3.8 | 1.3 | 0.0 | 0.0 |

*1Gradient means a gradient of an approximate straight line obtained from a comonomer content distribution profile.
*2CFC 1 means, in CFC, a gradient of an approximate straight line obtained from the relationship between an arbitrary temperature (falling within the range of between a first temperature at which a maximum amount of extraction is exhibited and a second temperature which is 10° C. higher than the first temperature) and a point on a molecular weight distribution profile of a copolymer fraction extracted at the arbitrary temperature at which point the molecular weight distribution profile exhibits a peak having a maximum intensity.
*3CFC 2 means a percent of the sum of respective amounts of copolymer fractions extracted at temperatures which are at least 10° C. lower than the above mentioned first temperature to the total amount of copolymer fractions as measured by CFC.

TABLE 2

|  |  | Example 1 | Comparative Example 1 | Comparative Example 2 | Comparative Example 3 | Comparative Example 4 | Comparative Example 5 | Comparative Example 6 | Comparitive Example 7 |
|---|---|---|---|---|---|---|---|---|---|
| Density | g/cm$^3$ | 0.929 | 0.883 | 0.926 | 0.912 | 0.910 | 0.912 | 0.905 | 0.930 |
| MFR | g/10 min | 0.50 | 0.35 | 2.1 | 4.5 | 2.9 | 3.9 | 1.3 | 0.015 |
| $M_w/M_n$ |  | 4.5 | 3.5 | 2.6 | 2.5 | 2.1 | 4.5 | 2.4 | 7.8 |
| Gradient*1 |  | 0.0013 | 0.0030 | −0.00005 | −0.00003 | −0.0007 | 0.0037 | −0.0013 | 0.0041 |
| CFC 1*2 |  | −0.053 | −0.010 | −0.006 | −0.033 | 0.000 | −0.016 | 0.000 | 0.005 |
| CFC 2*3 | wt % | 3.1 | 18.5 | 10.8 | 13.4 | 9.3 | 12.3 | 14.5 | 8.0 |

*1Gradient means a gradient of an approximate straight line obtained from a comonomer content distribution profile.
*2CFC 1 means, in CFC, a gradient of an approximate straight line obtained from the relationship between an arbitrary temperature (falling within the range of between a first temperature at which a maximum amount of extraction is exhibited and a second temperature which is 10° C. higher than the first temperature) and a point on a molecular weight distribution profile of a copolymer fraction extracted at the arbitrary temperature at which point the molecular weight distribution profile exhibits a peak having a maximum intensity.
*3CFC 2 means a percent of the sum of respective amounts of copolymer fractions extracted at temperatures which are at least 10° C. lower than the above mentioned first temperature to the total amount of copolymer fractions as measured by CFC.

TABLE 3

|  | Low Mw Component (Component II) | | | | High Mw Component (Component I) | | | |
|---|---|---|---|---|---|---|---|---|
| Example # | $I_2$ g/10 min | mole % butene | density g/cm$^3$ | wt % in blend | $I_2$ g/10 min | mole % butene | density g/cm$^3$ | wt % in blend |
| 9 | 25.96 | 1.42 | 0.9380 | 48 | 0.00872 | 5.96 | 0.9033 | 52 |
| 10 | 34.9 | 2.56 | 0.9378 | 48 | 0.01085 | 2.91 | 0.9148 | 52 |
| 11 | 31.6 | 4.99 | 0.9219 | 48 | 0.00194 | 1.45 | 0.9203 | 52 |
| 12 | 19.1 | 6.21 | 0.9210 | 48 | 0.01085 | 0 | 0.9484 | 52 |

TABLE 4

|  | Units | Example 9 | Example 10 | Example 11 | Example 12 |
|---|---|---|---|---|---|
| Melt Flow Properties |  |  |  |  |  |
| $I_2$ | g/10 min | 0.08 | 0.10 | 0.03 | 0.09 |
| $I_5$ | g/10 min | 0.25 | 0.32 | 0.11 | 0.28 |
| $I_{10}$ | g/10 min | 0.89 | 1.04 | 0.45 | 0.86 |
| $I_{21.6}$ | g/10 min | 4.89 | 5.5 | 2.47 | 3.83 |
| $I_{10}/I_2$ |  | 11.1 | 10.4 | 15 | 9.6 |
| $I_{21.6}/I_5$ |  | 19.6 | 17.2 | 22.5 | 13.7 |
| $I_{21.6}/I_2$ |  | 61.1 | 55 | 82.3 | 42.6 |
| Density | g/cm$^3$ | 0.9241 | 0.9273 | 0.9251 | 0.9376 |
| Butene Content | Mole % | 4 | 3.18 | 3.18 | 2.71 |

TABLE 4-continued

|  | Units | Example 9 | Example 10 | Example 11 | Example 12 |
|---|---|---|---|---|---|
| GPC Analysis |  |  |  |  |  |
| Mn | g/mole | 33700 | 32500 | 35500 | 37000 |
| Mw | g/mole | 203000 | 201000 | 279000 | 226000 |
| Mw/Mn | — | 6.02 | 6.18 | 7.86 | 6.11 |
| Rheology |  |  |  |  |  |
| Viscosity at 0.1 1/s | Pa·s | 69102 | 50522 | 124986 | 70364 |
| Viscosit at 100 1/s | Pa·s | 2656 | 2510 | 3273 | 337.2 |
| Mechanical Properties |  |  |  |  |  |
| Tensile Properties |  |  |  |  |  |
| Yield Stress | Mpa | 10.83 | 12.47 | 11.71 | 15.46 |
| Ultim. Stress | Mpa | 30.86 | 31.65 | 31.63 | 25.96 |
| Elongation | % | 617 | 704 | 764 | 882 |
| Toughness | Mpa | 102 | 124 | 133 | 148 |
| Slope SH | Mpa | 4.66 | 4.64 | 3.92 | 2.51 |
| 2% Sec. Mod. | Mpa | 216 | 309 | 244 | 446 |
| Young's Modulus | Mpa | 308 | 354 | 282 | 553 |
| Impact Properties |  |  |  |  |  |
| Gc + 0 C | kJ/m$^2$ | 76.4 | 18.6 | 35.1 | 21.5 |
| Gc −20 C | kJ/m$^2$ | 14.9 | 4.2 | 4.3 | 3.8 |
| PENT |  |  |  |  |  |
| 2.4 Mpa | Min. | >10$^5$ | >10$^5$ | >10$^5$ | 12 |
| Intrinsic Tear | g/mil. | 226 | 212 | 245 | 201 |
| Haze [0.5 mm] | % | 85.8 | 70.9 | 56.6 | 97.1 |

TABLE 5

|  |  | Low Mw Component (Component II) | | | High Mw Component (Component I) | | | |
|---|---|---|---|---|---|---|---|---|
| Example # | I$_2$ g/10 min | mole % 1-butene | density g/cm$^3$ | wt % in blend | I$_2$ g/10 min | mole % 1-butene | density g/cm$^3$ | wt % in blend |
| Example 13 | 67.3 | 0.01 | 0.9729 | 50 | 0.012 | 0.76 | 0.9295 | 50 |
| Example 14 | 380 | 0.01 | 0.9783 | 50 | 0.012 | 0.76 | 0.9295 | 50 |
| Example 15 | 380 | 0.01 | 0.9783 | 50 | 0.013 | 0.16 | 0.9378 | 50 |
| Example 16 | 380 | 0.01 | 0.9783 | 60 | 0.013 | 0.16 | 0.9378 | 40 |
| Comp. Ex. 8 | 113 | 0 | 0.9753 | 50 | 0.015 | 0.95 | 0.9306 | 50 |
| Comp. Ex. 9 | 280 | 0 | 0.9795 | 50 | 0.015 | 0.95 | 0.9306 | 50 |
| Comp. Ex. 10 | 280 | 0 | 0.9795 | 60 | 0.015 | 0.95 | 0.9306 | 40 |

TABLE 6

|  | Units | Example 13 | Example 14 | Example 15 | Example 16 | Comparative Ex. 8 | Comparative Ex. 9 | Comparative Ex. 10 |
|---|---|---|---|---|---|---|---|---|
| Melt Flow Properties |  |  |  |  |  |  |  |  |
| I$_2$ | g/10 min | 0.12 | 0.12 | 0.13 | 0.30 | 0.13 | 0.18 | 0.40 |
| I$_5$ | g/10 min | 0.51 | 0.49 | 0.45 | 1.29 | 0.54 | 0.74 | 1.84 |
| I$_{21.6}$ | g/10 min | 10.9 | 10.8 | 11.6 | 37.0 | 13.9 | 20.1 | 55.5 |
| I$_{21.6}$/I$_2$ |  | 90.8 | 89.8 | 92.0 | 125.5 | 109.5 | 111.4 | 139.1 |
| Density | g/cm$^3$ | 0.9550 | 0.9558 | 0.9611 | 0.9647 | 0.9551 | 0.9560 | 0.9603 |
| Impact Properties |  |  |  |  |  |  |  |  |
| Charpy +23 C | kgfcm/cm2 | 23.1 | 18.9 | 29.5 | 11.0 | 17.6 | 13.5 | 6.6 |
| Charpy −20 C | kgfcm/cm2 | 17.0 | 11.4 | 19.1 | 7.4 | 12.5 | 5.2 | 2.7 |
| ESCR Bending |  |  |  |  |  |  |  |  |
| 80 C | hr. | 1100 | >2,000 | 50 | 11 | 170 | 400 | 20 |
| 50 C | hr. | >2,000 | >2,000 | 330 | 140 | 1,000 | >2,000 | 360 |

What is claimed is:

1. An ethylene copolymer comprising repeating units of ethylene and at least one comonomer, selected from the group consisting of: (a) compounds represented by the formula $H_2C=CHR$, wherein R is a $C_1$-$C_{20}$ linear, branched or cyclic alkyl group or a $C_6$-$C_{20}$ aryl group, and (b) a $C_4$-$C_{20}$ diene, where the diene is linear, branched or cyclic, and wherein the ethylene copolymer has the following properties (1) to (5):

(1) a density d (g/cm³) of from 0.870 to 0.980;

(2) an $M_w/M_n$ from 2.5 to 10, wherein $M_w$ and $M_n$ are, respectively, a weight average molecular weight and a number average molecular weight, both as measured by gel permeation chromatography (GPC), and in addition, the $M_w/M_n$ satisfies the following inequalities: $1.25 \log M_w - 2.5 \leq M_w/M_n \leq 3.5 \log M_w - 11.0$;

(3) when, in cross fractionation chromatography (CFC) of the ethylene copolymer, with respect to extraction at an arbitrary temperature T(° C.), falling within the range between a first temperature, at which a maximum amount of extraction is exhibited, and a second temperature, which is 10° C. higher than the first temperature, the relationship between the arbitrary temperature T(° C.), and a point in molecular weight on a molecular weight distribution profile of a copolymer fraction extracted at the arbitrary temperature T(° C.), at which point in molecular weight, the molecular weight distribution profile of the copolymer fraction shows a peak having a maximum intensity, is treated by the least squares method to obtain an approximate straight line, and wherein the approximate straight line has a gradient within the range defined by the formula (I):

$$-1 \leq \{\log Mp(T^1) - \log Mp(T^2)\}/(T^1 - T^2) \leq -0.005 \quad (I)$$

wherein:

$T^1$ and $T^2$ are two different arbitrary extraction temperatures T(° C.) within the range between the first temperature and the second temperature, and $Mp(T^1)$ and $Mp(T^2)$ are, respectively, molecular weights corresponding to $T^1$ and $T^2$ on the approximate straight line; and (4) the measurement of the ethylene copolymer by CFC shows characteristics, such that the sum of respective amounts of copolymer fractions extracted at temperatures, which are at least 10° C. lower than the first temperature, as defined above, is 8% by weight or less, based on the total amount of, excluding purge, copolymer fractions extracted at temperatures in the overall range of extraction temperatures in CFC;

(5) within a range in molecular weight of the ethylene copolymer, which is defined by the formula (II):

$$\log(Mt) - \log(Mc) \leq 0.5 \quad (II),$$

wherein:

Mt is a point in molecular weight on a molecular weight distribution profile at which the profile shows a peak having a maximum intensity, and Mc is an arbitrary point in molecular weight on the molecular weight distribution profile, the molecular weight distribution profile is obtained, together with a comonomer content distribution profile, by subjecting the ethylene copolymer to gel permeation chromatography/Fourier transformation infrared spectroscopy (GPC/FT-IR), and an approximate straight line, obtained from the comonomer content distribution profile by the least squares method, has a gradient within the range defined by the formula (III):

$$0.0005 \leq \{C(Mc^1) - C(Mc^2)\}/(\log Mc^1 - \log Mc^2) \leq 0.05 \quad (III)$$

wherein:

$Mc^1$ and $Mc^2$ are two different arbitrary points (Mc) in molecular weight, which satisfy the formula (II), and $C(Mc^1)$ and $C(Mc^2)$ are, respectively, comonomer contents corresponding to $Mc^1$ and $Mc^2$ on the approximate straight line; and wherein the ethylene copolymer is prepared in the presence of a transition metal compound which contains only one cyclic π-bonded anionic ligand.

2. The ethylene copolymer according to claim 1, wherein the ethylene copolymer is characterized as having the following properties:

a) a density from 0.915 to 0.955 g/cm³;
b) a melt index ($I_2$) from 0.01 to 3000 g/10 min;
c) an $I_{10}/I_2$ from 5.5 to 25; and
d) an $M_w/M_n$ from 3 to 7.

3. The ethylene copolymer of claim 1, wherein the at least one comonomer is selected from the group consisting of propylene, 1-butene, 1-pentene, 1-hexene, 4-methyl-1-pentene, 1-octene, 1-decene, 1-dodecene, 1-tetradecene, 1-hexadecene, 1-octadecene and 1-eicosene.

4. The ethylene copolymer of claim 1, wherein the at least one comonomer is selected from the group consisting of 1,3-butadiene, 1,4-pentadiene, 1,4-hexadiene, 1,5-hexadiene and cyclohexadiene.

5. A composition comprising the ethylene copolymer of claim 1 and one or more additives.

6. A composition comprising the ethylene copolymer of claim 1 and a homogeneous, narrow composition distribution ethylene/α-olefin interpolymer.

7. A composition comprising the ethylene copolymer of claim 1 and a heterogeneous, broad composition distribution ethylene/α-olefin interpolymer.

8. A composition comprising the ethylene copolymer of claim 1 and a homopolymer.

9. A fabricated article formed from a composition comprising the ethylene copolymer of claim 1, and wherein the article is in the form of a fiber, a foam, a sheet, a molded article, or a coating.

10. The fabricated article of claim 9, wherein the article is formed from a thermoforming, a blow molding, or an injection molding process.

11. The fabricated article of claim 9, wherein the article is selected from the group consisting of pipes, tubing, cable or wire jackets, pipe coatings, geomembranes, thermoformed articles, stackable plastic pallets, blow molded bottles or containers, and environmental pond liners.

12. A geomembrane formed from a composition comprising an ethylene copolymer, comprising repeating units of ethylene and at least one comonomer, selected from the group consisting of: (a) compounds represented by the formula $H_2C=CHR$, wherein R is a $C_1$-$C_{20}$ linear, branched or cyclic alkyl group or a $C_6$-$C_{20}$ aryl group, and (b) a $C_4$-$C_{20}$ diene, where the diene is linear, branched or cyclic, and wherein the ethylene copolymer is characterized by a molecular weight maximum occurring in a fraction of said copolymer with the highest comonomer content; and wherein composition further comprises a heterogeneous, broad composition distribution ethylene/α-olefin interpolymer.

* * * * *